US009055911B2

(12) United States Patent
Sakuragi et al.

(10) Patent No.: US 9,055,911 B2
(45) Date of Patent: Jun. 16, 2015

(54) RADIATION GENERATING DEVICE AND RADIATION IMAGING APPARATUS

(71) Applicant: CANON KABUSHIKI KAISHA, Tokyo (JP)

(72) Inventors: Shichihei Sakuragi, Tokyo (JP); Satoru Omura, Chigasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 68 days.

(21) Appl. No.: 14/075,235

(22) Filed: Nov. 8, 2013

(65) Prior Publication Data

US 2014/0133627 A1    May 15, 2014

(30) Foreign Application Priority Data

Nov. 12, 2012  (JP) .................. 2012-248612
Mar. 29, 2013  (JP) .................. 2013-073413

(51) Int. Cl.
*A61B 6/00*    (2006.01)

(52) U.S. Cl.
CPC ............. *A61B 6/4405* (2013.01); *A61B 6/4291* (2013.01); *A61B 6/4429* (2013.01); *A61B 6/4452* (2013.01); *A61B 6/447* (2013.01); *A61B 6/547* (2013.01); *A61B 6/56* (2013.01); *A61B 6/588* (2013.01)

(58) Field of Classification Search
USPC .................................... 378/198, 197
See application file for complete search history.

(56) References Cited

U.S. PATENT DOCUMENTS

| | | | |
|---|---|---|---|
| 5,628,327 A * | 5/1997 | Unger et al. ............. | 600/562 |
| 2013/0140412 A1* | 6/2013 | Hirose ................. | 248/124.1 |
| 2014/0098939 A1* | 4/2014 | Yamanaka, Shinji ....... | 378/62 |

FOREIGN PATENT DOCUMENTS

| | | |
|---|---|---|
| JP | 2007144161 A | 6/2007 |
| JP | 2010057546 A | 3/2010 |
| JP | 2012065947 A | 4/2012 |

* cited by examiner

*Primary Examiner* — Kiet T Nguyen
(74) *Attorney, Agent, or Firm* — Canon USA Inc. IP Division

(57) ABSTRACT

A radiation imaging apparatus includes an arm configured to support a radiation generating unit that generates radiation, a post configured to support the arm, a movable portion configured to support the post and to be movable on a floor, and a supporting foot portion that is rotatable with respect to the movable portion. The supporting foot portion and the arm are operable to be placed in an open state and a closed state. In a state where the supporting foot portion and the arm are closed, the supporting foot portion covers the radiation generating unit.

21 Claims, 20 Drawing Sheets

FIG. 1A
FIG. 1B
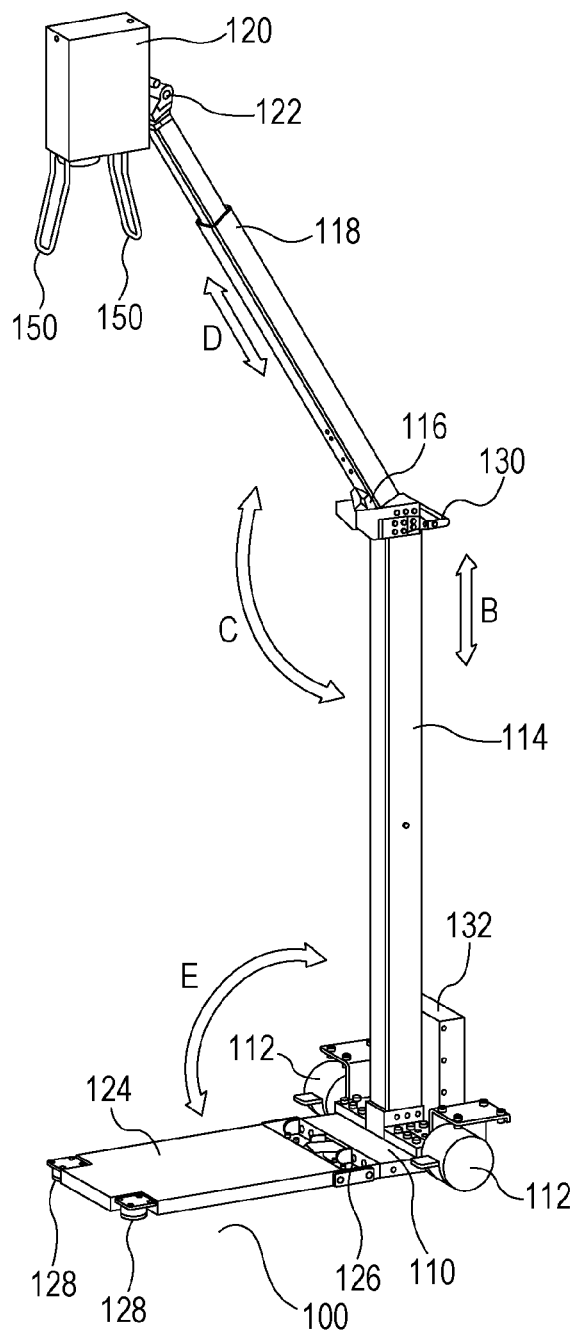
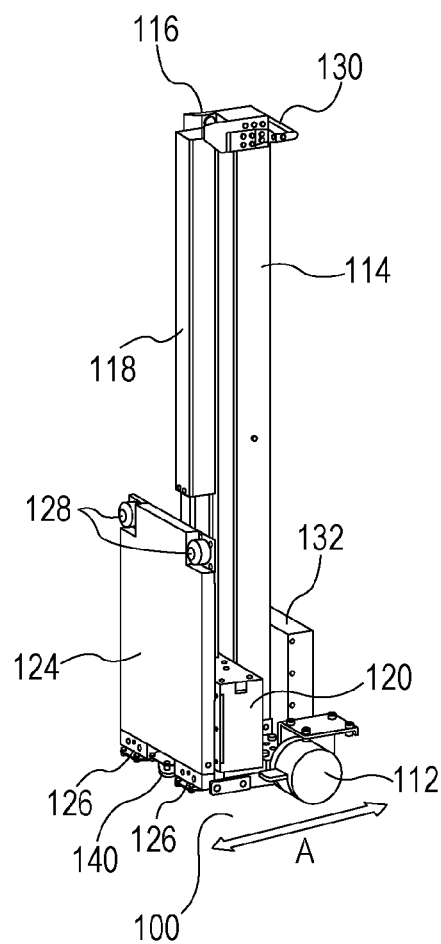

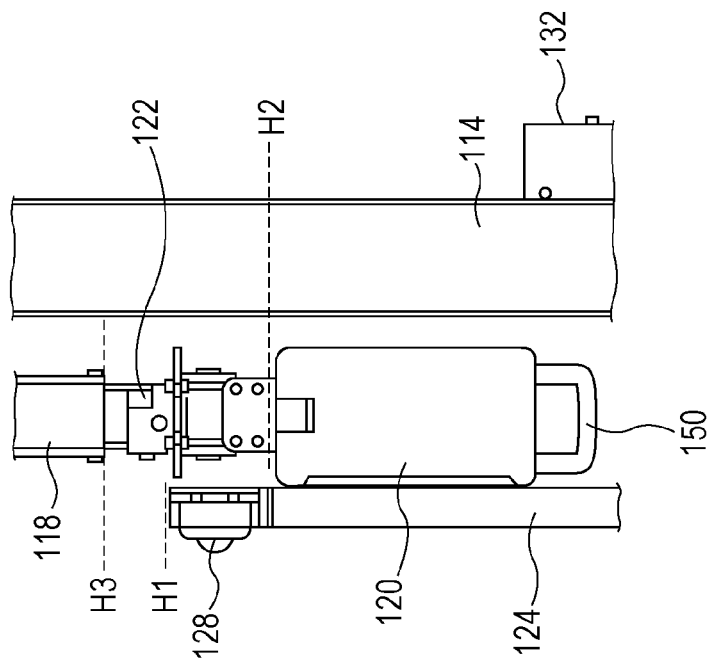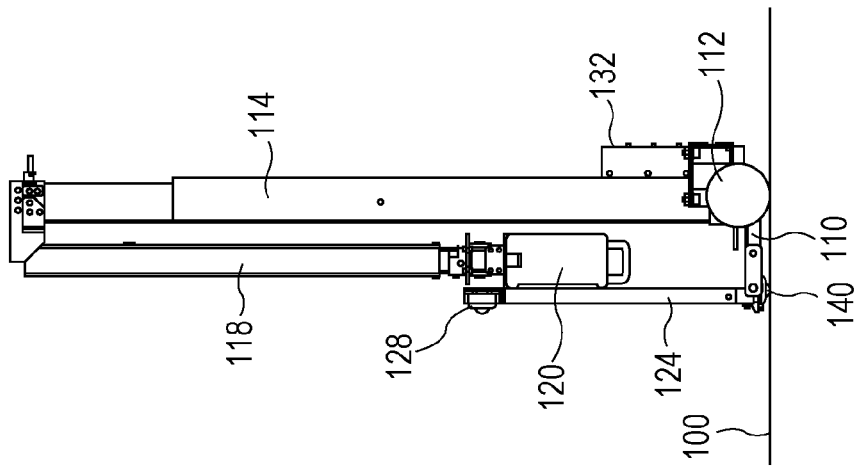

RADIATION GENERATING DEVICE AND RADIATION IMAGING APPARATUS

BACKGROUND OF THE INVENTION

1. Field of the Invention

The present invention generally relates to a radiation generating device and a radiation imaging apparatus each including a radiation generating unit configured to emit radiation toward a subject. More particularly, the present invention relates to a movable radiation imaging apparatus including a radiation generating unit.

2. Description of the Related Art

Movable radiation imaging apparatuses that are portable are known. To perform imaging with such a portable radiation imaging apparatus, the apparatus needs to include a radiation generating unit that is provided at a high position and a supporting member that allows the radiation generating unit to be moved to any position in accordance with the site (location or posture) of a subject that is to be imaged. Hence, for example, Japanese Patent Laid-Open No. 2007-144161 discloses a radiation imaging apparatus including an arm that supports a radiation generating unit and a post that supports the arm, the arm being rotatably connected to the post. Other exemplary radiation imaging apparatuses are disclosed by Japanese Patent Laid-Open No. 2012-65947 and Japanese Patent Laid-Open No. 2010-57546.

The radiation imaging apparatus disclosed by Japanese Patent Laid-Open No. 2007-144161 may be difficult to carry because only the arm is rotatable. Hence, further improvements are expected to be made.

SUMMARY OF THE INVENTION

The various embodiments disclosed in the present invention provides a radiation generating device and a radiation imaging apparatus that offer improved portability, and are easier to use and handle than previously known counterparts.

According to an aspect of the present invention, a radiation generating device includes an arm configured to support a radiation generating unit that generates radiation, a post configured to support the arm, a movable portion configured to support the post and to be movable on a floor, and a supporting foot portion that is rotatable with respect to the movable portion.

According to the above aspect of the present invention, the radiation imaging apparatus is well balanced during an imaging operation and is easy to carry during transportation. Thus, characteristics of the apparatus such as usability, portability, and so forth are effectively improved.

Further features of the present invention will be apparent from the following description of exemplary embodiments with reference to the attached drawings.

BRIEF DESCRIPTION OF THE DRAWINGS

FIGS. 1A and 1B illustrate an overall configuration of a transportable radiation generating device according to a first embodiment of the present invention.

FIGS. 10A and 10B illustrate the radiation generating device in yet a further exemplary state of extension and contraction according to the first embodiment.

DESCRIPTION OF THE EMBODIMENTS

Figure 2:
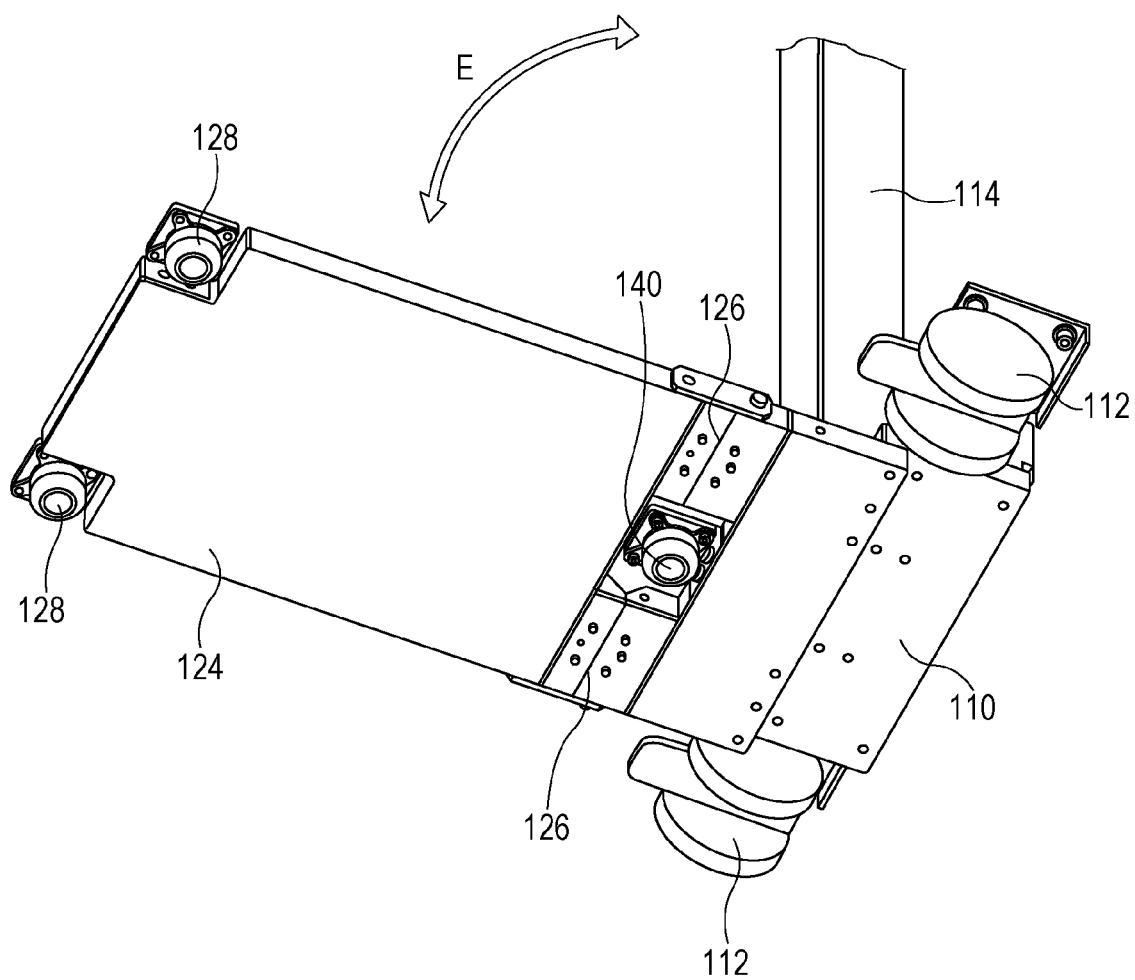
FIG. 2 illustrates the underside of the radiation generating device according to the first embodiment.

Exemplary embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

FIGS. 1A and 1B illustrate a configuration of a radiation generating device according to a first embodiment of the present invention. FIG. 1A is a perspective view of the radiation generating device that is ready for imaging. FIG. 1B is a perspective view of the radiation generating device that is ready to be transported or carried.

The radiation generating device includes a movable portion 110 provided with wheels 112, and a post 114 standing vertically on the movable portion 110. The radiation generating device further includes an arm 118 rotatably attached to the post 114, a radiation generating unit 120 rotatably attached to the arm 118 and configured to generate radiation, and a supporting foot portion 124 operable to be opened and closed with respect to the movable portion 110. To make the radiation generating device as compact as possible, the radiation generating device according to the first embodiment does not include a display device that displays an image.

The wheels 112 provided to the movable portion 110 are rotatable on a floor 100. The wheels 112, which are a plurality of tires or casters, are constantly in contact with the floor 100. When the wheels 112 are rotated in the state illustrated in FIG. 1B, the radiation generating device including the movable portion 110 moves in the anteroposterior direction (a direction of arrow A in FIG. 1B).

The post 114 is provided on the movable portion 110. The movable portion 110 may form part of the post 114. The post 114 stands vertically on the movable portion 110. The post 114 has a predetermined length and includes an extension mechanism that allows the post 114 to extend and contract in its longitudinal direction. That is, the post 114 is extendable and contractible in the vertical direction (a direction of arrow B in FIG. 1A). A specific example of the extension mechanism included in the post 114 will be described separately below.

The post 114 is provided with a handle 130 to be gripped by an operator when the operator carries the radiation generating device from one place to another. As illustrated in FIGS. 1A and 1B, the handle 130 is provided at the upper end of the post 114. The operator grips the handle 130 and pulls the handle 130 in a direction in which the movable portion 110 is movable, whereby the movable portion 110 is moved and thus the radiation generating device is carried. The handle 130 is provided at the upper end of the post 114. Therefore, when the post 114 is extended or contracted in the vertical direction (the direction of arrow B), the handle 130 is moved in the vertical direction (the direction of arrow B). That is, the position of the handle 130 is adjustable by extending or contracting the post 114. This is beneficial to accommodate of different height and strength.

As illustrated in FIG. 1A, a control unit 132 configured to control an exposure operation of the radiation generating unit 120 is provided at the lower end of the post 114. The control unit 132 is provided as an integral part of the post 114. Alternatively, the control unit 132 may be provided on the movable portion 110. The control unit 132 is provided on a side of the post 114 on which the handle 130 is provided. The control unit 132 is generally heavier than the other elements, such as the radiation generating unit 120. Therefore, providing the control unit 132 at the lower end of the post 114 (or on the movable portion 110 or at a position near the floor 100) stabilizes the balance of the radiation generating device. The control unit 132 may include a central processing unit (CPU) with control modules and circuitry configured to control the imaging operation of the radiation generating unit 120. The control unit 132 may also include a power supply unit, such as a battery, that supplies power to the radiation generating unit 120.

The radiation generating unit 120 is of a transmission type. In a transmission radiation generating unit, radiation blocking members are provided on a side of a target on which electrons are incident and on a side of the target from which radiation is emitted, respectively, so that unnecessary radiation is blocked. In the transmission radiation generating unit, the entirety of a radiation generating tube or an envelope that houses the radiation generating tube does not need to be enclosed by a blocking member that is made of lead or the like. Therefore, the transmission radiation generating unit can be made smaller and lighter than, for example, a radiation generating unit employing a rotating anode.

The arm 118 is connected to the radiation generating unit 120 at one end thereof and to the post 114 at the other end thereof. The arm 118 supports the radiation generating unit 120 and has a predetermined length. As illustrated in FIG. 1A, the arm 118 includes an extension mechanism that allows the arm 118 to telescopically extend and contract in its longitudinal direction (a direction of arrow D in FIG. 1A). That is, the arm 118 is capable of moving the radiation generating unit 120 in its longitudinal direction (the direction of arrow D). Hence, when the arm 118 is extended in the predetermined direction (the direction of arrow D), the radiation generating unit 120 is moved toward a subject. A specific example of the extension mechanism included in the arm 118 will be described separately below.

The arm 118 is rotatable about the upper end of the post 114. Specifically, as illustrated in FIG. 1A, the post 114 is provided with an arm hinge portion 116 that allows the arm 118 to rotate in a predetermined direction (a direction of arrow C in FIG. 1A). The arm 118 is rotatable within a predetermined range (about 180 degrees) in the predetermined direction (the direction of arrow C). The arm 118 is rotatable on a side of the post 114 that is opposite the side on which the handle 130 and the control unit 132 are provided.

The arm hinge portion 116 includes a mechanism that connects the arm 118 and the post 114 to each other and allows the arm 118 to be opened and closed with respect to the post 114. When the arm 118 is closed, the arm 118 extends substantially parallel to the post 114.

As described above, the arm hinge portion 116 changes its form when the arm 118 is rotated in the predetermined direction (the direction of arrow C), that is, from a form in which the arm 118 is extendable and contractible upward and downward or leftward and rightward as illustrated in FIG. 1A to a form in which the arm 118 is tucked away together with the radiation generating unit 120 as illustrated in FIG. 1B. The form in which the arm 118 is extendable and contractible upward and downward or leftward and rightward as illustrated in FIG. 1A refers to a state where the radiation generating unit 120 is movable toward the subject. The form in which the arm 118 is tucked away together with the radiation generating unit 120 as illustrated in FIG. 1B refers to a state where the arm 118 has been closed in such a manner as to extend substantially parallel to the post 114, that is, a state where the radiation generating unit 120 is positioned near the floor 100.

A rotational portion 122 that allows the radiation generating unit 120 to rotate is provided between the radiation generating unit 120 and the arm 118. The radiation generating unit 120 is rotated so as to be positioned with respect to the subject. Thus, radiation is emitted in a desired direction. A specific example of the rotational portion 122 will be described separately below.

The supporting foot portion 124 supports the radiation generating device. In the form illustrated in FIG. 1B, only the movable portion 110, including the wheels 112, among the elements of the radiation generating device is in contact with the floor 100. In the form illustrated in FIG. 1A, the movable portion 110, including the wheels 112, and the supporting foot portion 124 among the elements of the radiation generating device are in contact with the floor 100. That is, the movable portion 110, including the wheels 112, and the supporting foot portion 124 in combination support the radiation generating device. With the presence of the supporting foot portion 124, the area of contact between the radiation generating device and the floor 100 is increased. Hence, for example, in a state where the radiation generating unit 120 has been positioned with respect to the subject, the radiation generating device is balanced by the supporting foot portion 124. Since the radiation generating unit 120 is of a transmission type, no heavy carriage is necessary. Even if the supporting foot portion 124 is openable and closable, the radiation generating device is balanced.

Specifically, the supporting foot portion 124 is a plate-like member and includes pads 128 that support the radiation generating device by being in contact with the floor 100. The supporting foot portion 124 has a face having a larger area than any of the faces of the radiation generating unit 120. The pads 128 are provided on the underside of the supporting foot portion 124. The pads 128 may be movable members such as a plurality of tires or casters that are movable on the floor 100. The supporting foot portion 124 is rotatable in a predetermined direction (a direction of arrow E in FIG. 1A) in such a manner as to be opened and closed with respect to the movable portion 110. The supporting foot portion 124 is rotatable on a side of the post 114 that is opposite the side having the control unit 132. The supporting foot portion 124 is rotatable within about 90 degrees in the predetermined direction (the direction of arrow E). The axis of rotation of the supporting foot portion 124 is parallel to the axis of rotation of the arm 118.

Specifically, the supporting foot portion 124 is connected to the movable portion 110 with a supporting-foot hinge portion 126 interposed therebetween. The supporting foot portion 124 is openable and closable with the aid of the supporting-foot hinge portion 126. To perform imaging, the operator opens the supporting foot portion 124 as illustrated in FIG. 1A, whereby the radiation generating device is supported by the supporting foot portion 124 and the movable portion 110. In this state, the supporting foot portion 124 and the movable portion 110 form an integral body with the aid of the supporting-foot hinge portion 126. The supporting-foot hinge portion 126 includes a lock mechanism that connects and locks the supporting foot portion 124 and the movable portion 110 to each other.

To carry the radiation generating device, the operator first tucks away the arm 118 together with the radiation generating unit 120 as illustrated in FIG. 1B. Subsequently, the operator unlocks the supporting foot portion 124 and the movable portion 110 that have been locked by the supporting-foot hinge portion 126, and closes the supporting foot portion 124. Since the supporting foot portion 124 has a face having a larger area than any of the faces of the radiation generating unit 120, the supporting foot portion 124 covers the radiation generating unit 120. That is, in the state where the supporting foot portion 124 and the arm 118 are closed, the supporting foot portion 124 covers the radiation generating unit 120.

Hence, the supporting foot portion 124 functions as a cover for the radiation generating unit 120 and thus protects the radiation generating unit 120. In the state where the supporting foot portion 124 and the arm 118 are closed, all elements of the radiation generating device are positioned on the movable portion 110. That is, the radiation generating device is supported only by the movable portion 110.

When the radiation generating device is ready to be carried (in the state where the supporting foot portion 124 and the arm 118 are closed), the radiation generating unit 120 and the control unit 132, which are heavy elements, are positioned near the floor 100. Therefore, the radiation generating device has its center of gravity at a low position. Specifically, the radiation generating unit 120 is positioned nearer to the floor 100 than the upper end of the supporting foot portion 124 that is in the closed state. Thus, the radiation generating device is balanced, and the force required for tilting the radiation generating device by gripping the handle 130 in carrying the radiation generating device is reduced.

FIG. 2 mainly illustrates the undersides of the movable portion 110 and the supporting foot portion 124. The wheels 112 are provided on two respective sides of the movable portion 110. Each of the wheels 112 has a lock mechanism configured to stop the rotation thereof. In addition to the wheels 112, a pad 140 is provided to the movable portion 110. The pad 140 supports the radiation generating device by being in contact with the floor 100. The pad 140 may include a plurality of movable members such as tires or casters. The pads 128 are provided on the underside of the supporting foot portion 124. In the state where the supporting foot portion 124 is opened as illustrated in FIG. 2, the radiation generating device is supported by the pads 128 of the supporting foot portion 124 and the wheels 112 of the movable portion 110. That is, the radiation generating device is supported at four points, i.e., the two pads 128 and the two wheels 112.

In the state where the supporting foot portion 124 is closed as illustrated in FIG. 1B, the radiation generating device is supported by the pad 140 of the movable portion 110 and the wheels 112 of the movable portion 110. That is, the radiation generating device is supported at three points, i.e., the one pad 140 and the two wheels 112. In the state where the supporting foot portion 124 is opened, at least the two pads 128 and the wheels 112 of the movable portion 110 are in contact with the floor 100, while the pad 140 may be out of contact with the floor 100. The pad 140 functions as a contact point at least in the state where the radiation generating device is ready to be carried. The pad 140 may be a projection.

Figure 3:
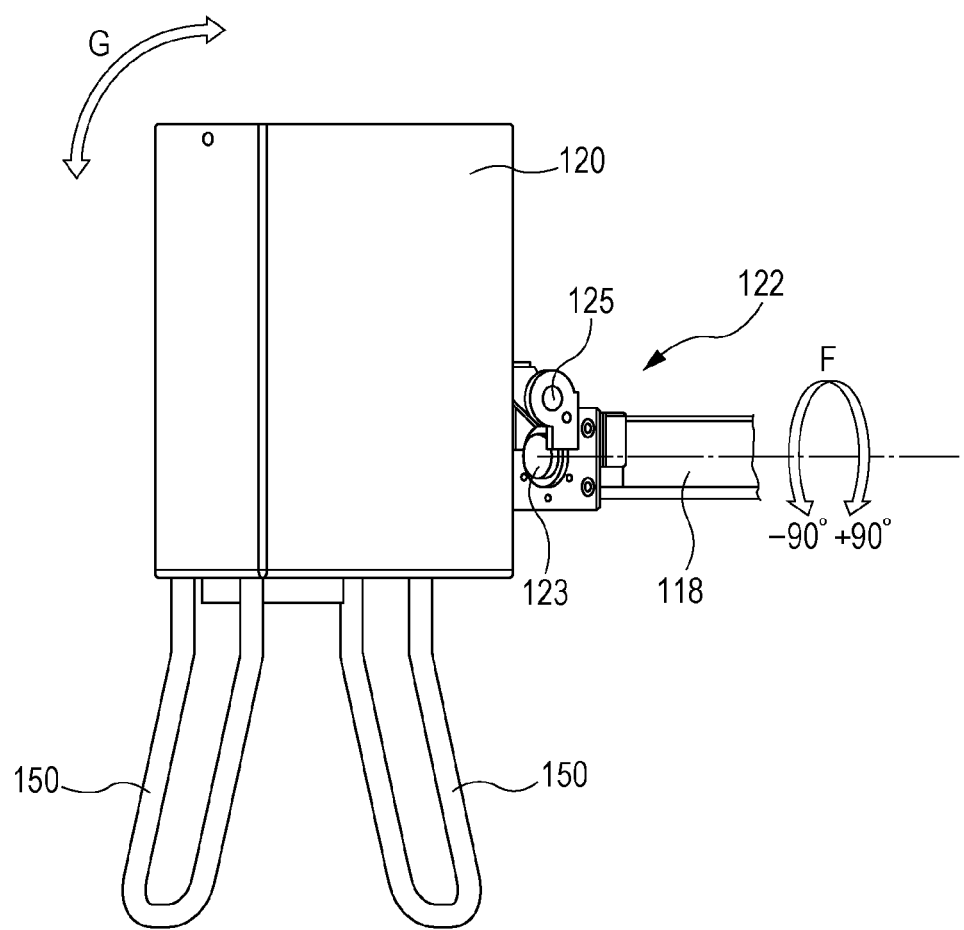
FIG. 3 illustrates a rotational portion of the radiation generating device according to the first embodiment.

FIG. 3 illustrates a specific example of the rotational portion 122 that allows the radiation generating unit 120 to rotate. The rotational portion 122 includes a swivel hinge 123 that allows the radiation generating unit 120 to rotate about an axis that is parallel to the longitudinal direction of the arm 118, and a tilt hinge 125 that allows the radiation generating unit 120 to rotate about an axis that is perpendicular to the longitudinal direction of the arm 118. The swivel hinge 123 is provided on a side of the rotational portion 122 that is connected to the arm 118. The tilt hinge 125 is provided on a side of the rotational portion 122 that is connected to the radiation generating unit 120.

With the aid of the swivel hinge 123, the radiation generating unit 120 is rotatable in the predetermined direction (a direction of arrow F in FIG. 3). The direction of emission from the radiation generating unit 120 is changeable at least within a range of −90 degrees to 90 degrees with the arm 118 extending horizontally and the direction of emission from the radiation generating unit 120 being oriented toward the floor 100. With the aid of the tilt hinge 125, the radiation generating unit 120 is rotatable in the predetermined direction (a direction of arrow G in FIG. 3). The axis of rotation, in the direction of arrow F, of the swivel hinge 123 coincides with the axis of the arm 118. The axis of rotation, in the direction of arrow F, of the swivel hinge 123 is orthogonal to the axis of rotation, in the direction of arrow G, of the tilt hinge 125. By allowing the rotation of the radiation generating unit 120 with the aid of the tilt hinge 125, the radiation generating unit 120 is tiltable at such an angle that the direction of emission from the radiation generating unit 120 is vertical to the floor 100, even if the arm 118 is at any angle with respect to the post 114.

To move the radiation generating unit 120 from the position for imaging as illustrated in FIG. 1A to the position for carrying as illustrated in FIG. 1B, the radiation generating unit 120 is rotated about the swivel hinge 123 and the tilt hinge 125. Thus, the radiation generating unit 120 is tucked between the post 114 and the supporting foot portion 124. In the state where the arm 118 is closed and the radiation generating unit 120 is tucked away, the direction of emission from the radiation generating unit 120 is horizontal.

The swivel hinge 123 and the tilt hinge 125 are operable independently of each other. The swivel hinge 123 and the tilt hinge 125 may each be a torque hinge that is capable of freely changing and retaining the orientation of the radiation generating unit 120. For example, the swivel hinge 123 and the tilt hinge 125 may each be a torque hinge or a damper hinge having a small torque and including a lock mechanism capable of locking the hinge at any angle. Moreover, the swivel hinge 123 and the tilt hinge 125 may each include a lock mechanism that is capable of locking the radiation generating unit 120 only in desired orientations.

The radiation generating unit 120 has a pair of guide members 150 functioning as assist members that keep the radiation generating unit 120 at a predetermined distance from the subject. The operator grips, lifts, or pulls one or both of the guide members 150, thereby moving the radiation generating unit 120 to a desired position.

Figure 4:
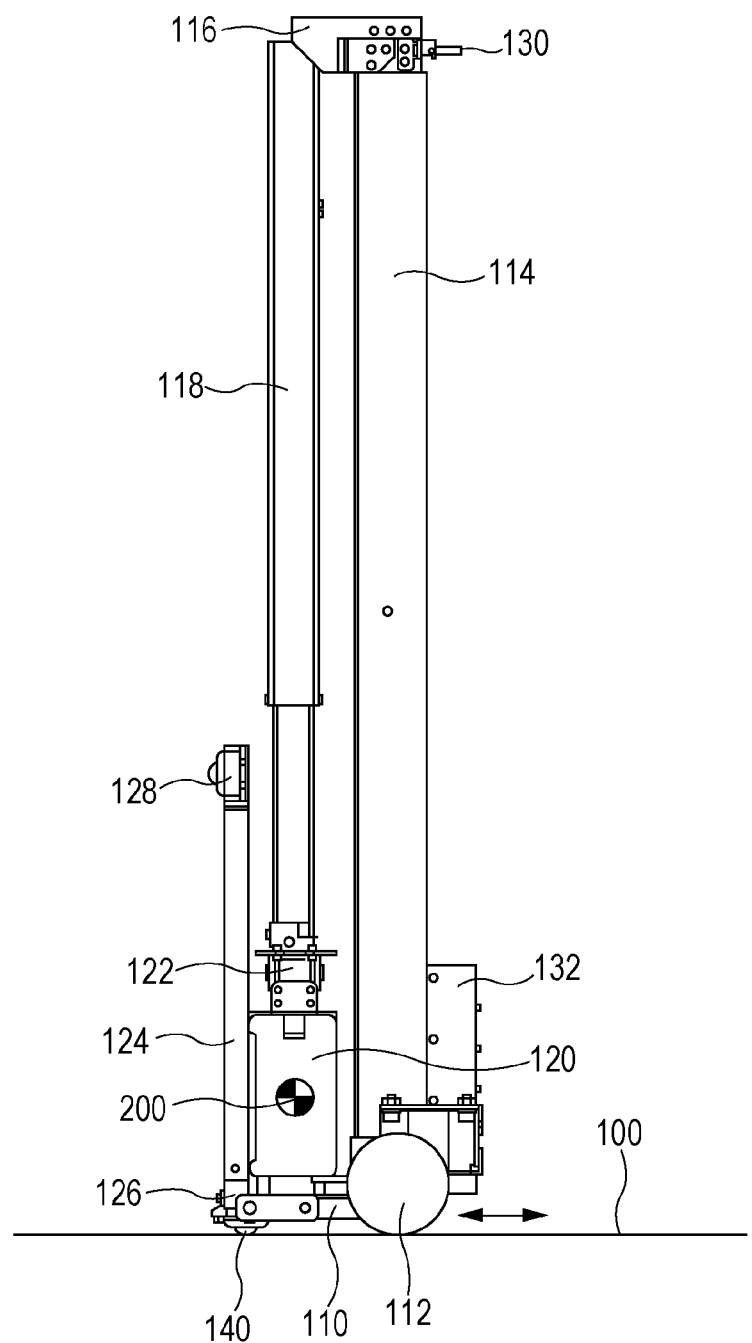
FIG. 4 illustrates the radiation generating device in a collapsed or tucked state.

As illustrated in FIG. 4, to carry the radiation generating device, the radiation generating unit 120 is tucked away by closing the arm 118. In this state, the radiation generating unit 120 resides between the post 114 and the supporting foot portion 124. The center of gravity of the radiation generating unit 120 resides at a position near the movable portion 110, i.e., a position near the floor 100. The position near the movable portion 110 refers to, for example, a position at 20 cm or less from the movable portion 110. The position near the floor 100 refers to, for example, a position at 30 cm or less from the floor 100. In FIG. 4, the center of gravity of the radiation generating unit 120 is denoted by 200. The radiation generating unit 120 is of a transmission type and is therefore of a small size. Hence, the radiation generating unit 120 is tuckable between the post 114 and the supporting foot portion 124. The center of gravity 200 of the radiation generating unit 120 when the radiation generating unit 120 is at the position for carrying resides above and inside a polygon defined by the contact points between the floor 100 and the wheels 112 and the pad 140 of the movable portion 110.

In the horizontal direction (the lateral direction in FIG. 4) in which the movable portion 110 is movable, the radiation generating unit 120 is positioned between the pad 140 and the wheels 112 of the movable portion 110. The supporting foot portion 124, a set of the radiation generating unit 120 and the arm 118, the post 114, and the control unit 132 are arranged in that order from the left on the movable portion 110. The arm 118 and the post 114 are longer than the other elements of the radiation generating device. The arm 118 and the post 114 are provided on a central part of the movable portion 110 while being held between the supporting foot portion 124 and the control unit 132, whereby the radiation generating device is balanced. The radiation generating unit 120 and the control unit 132 are heavier than the other elements of the radiation generating device. In the state where the radiation generating unit 120 is tucked away, the radiation generating unit 120 and the control unit 132 are positioned near the floor 100, whereby the radiation generating device is balanced.

In the state where the arm 118 is closed and the radiation generating unit 120 is tucked away, the center of gravity 200 of the radiation generating unit 120 resides between the pad 140 and the wheels 112 of the movable portion 110. In the vertical direction, the radiation generating unit 120 is positioned on the movable portion 110 while the centers of gravity of the arm 118 and the post 114 reside between the pad 140 and the wheels 112 of the movable portion 110.

In the state where the arm 118 is closed and the radiation generating unit 120 is tucked away, the post 114, the arm 118, and the supporting foot portion 124 extend substantially parallel to one another. The post 114 is longer than the arm 118 and the radiation generating unit 120. Hence, in closing the arm 118 so as to tuck away the radiation generating unit 120, the radiation generating unit 120 does not interfere with the movable portion 110.

Figure 5:
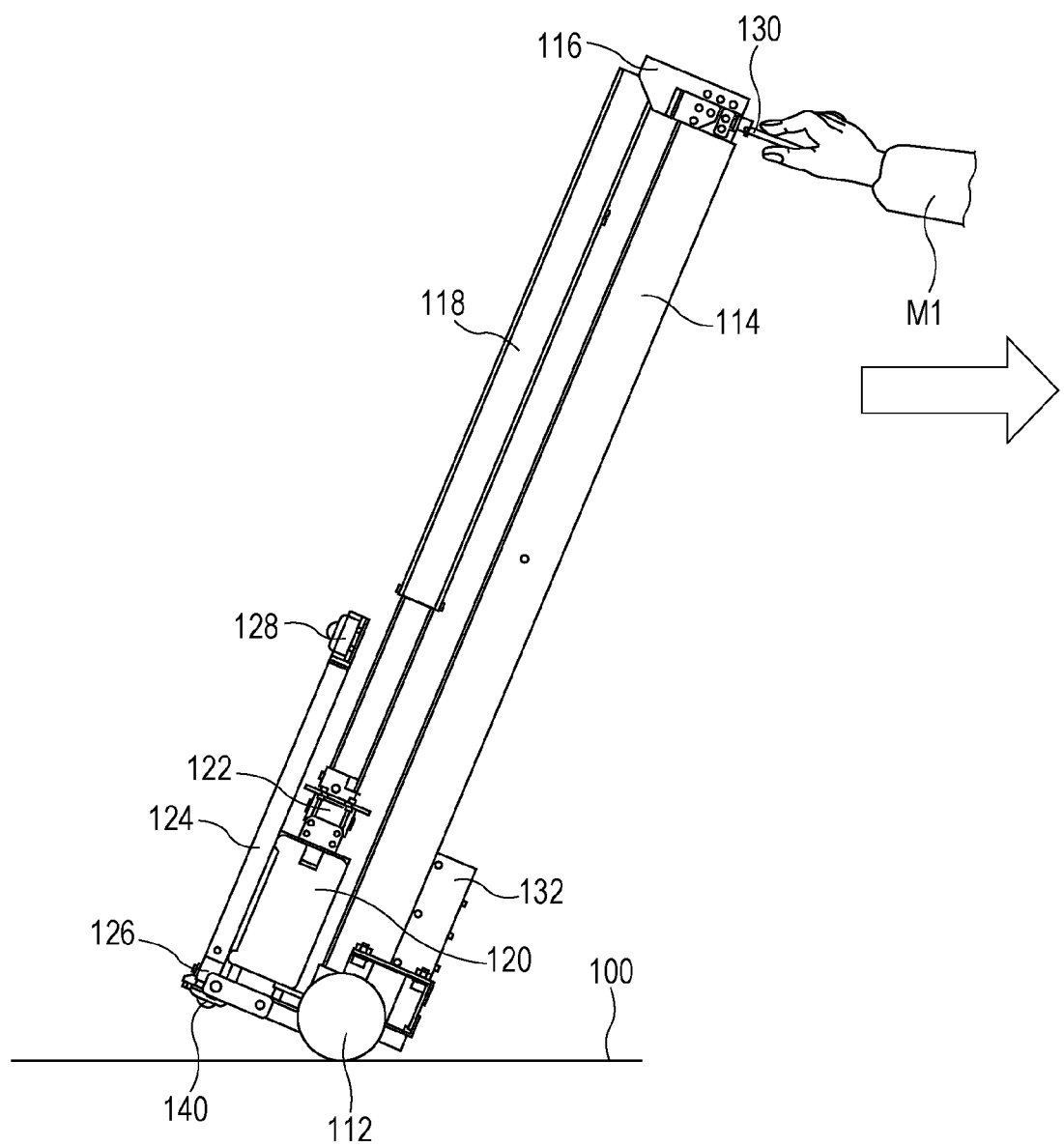
FIG. 5 illustrates an example of the manner in which the radiation generating device is carried or transported between different locations.

When the radiation generating device is ready to be carried, the radiation generating device stands upright as illustrated in FIG. 4. In this state, the operator first disables the lock mechanism that is locking the rotation of the wheels 112. Then, as illustrated in FIG. 5, the operator grips the handle 130 with a hand M1. Subsequently, the operator pulls the handle 130 in a direction in which the operator wants to move the radiation generating device. FIG. 5 illustrates a case where the handle 130 is pulled to the right side of the page. In this state, the radiation generating device is tilted, and only the wheels 112 of the movable portion 110 are in contact with the floor 100 and rotate. With the rotation of the wheels 112, the radiation generating device moves to the right. When the radiation generating device has been moved to a desired position, the operator takes the hand M1 off the handle 130. Thus, the radiation generating device stands upright as illustrated in FIG. 4.

Figure 6:
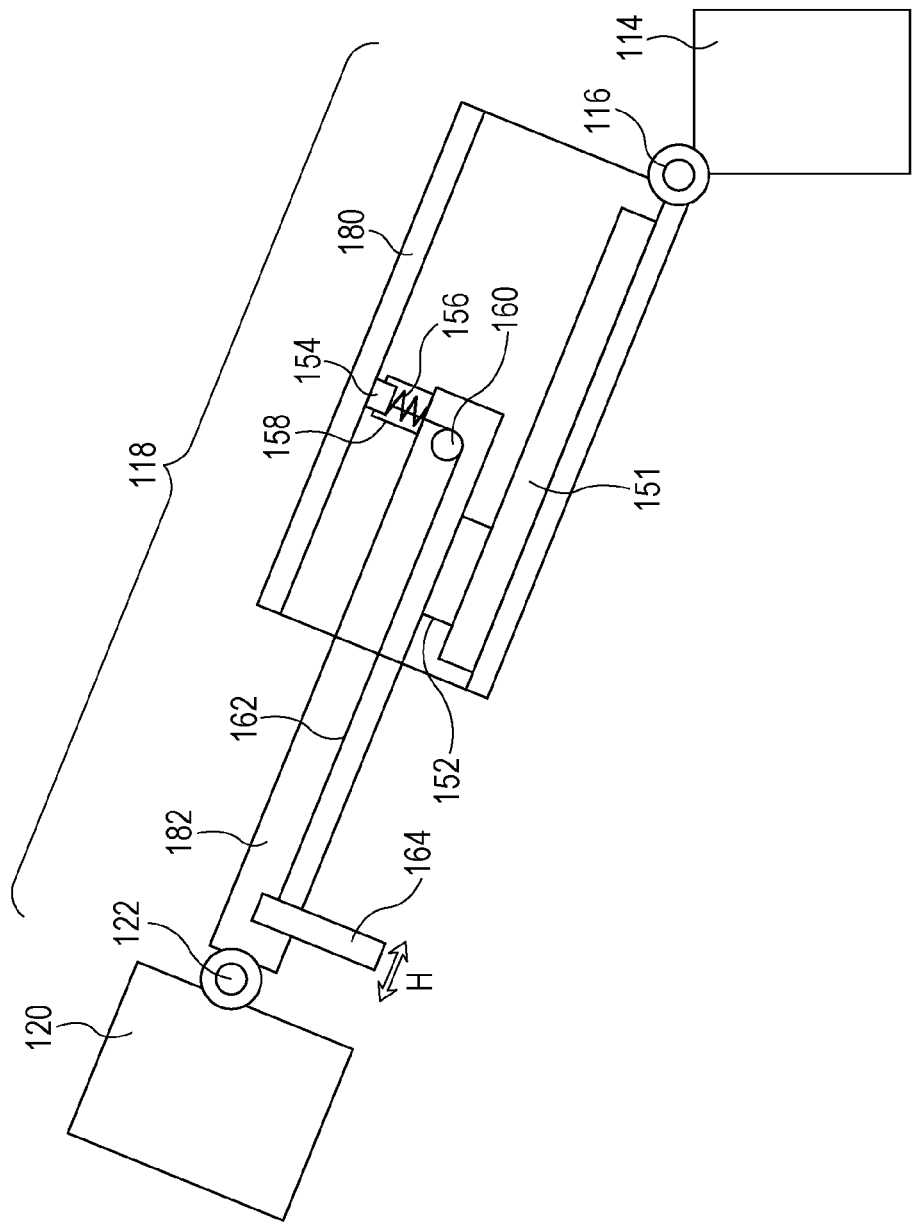
FIG. 6 illustrates an extension mechanism included in an arm of the radiation generating device according to the first embodiment.

A specific example of the extension mechanism included in the arm 118 will now be described with reference to FIG. 6. The arm 118 includes a fixed arm 180 and a movable arm 182 that is movable with respect to the fixed arm 180. The fixed arm 180 and the movable arm 182 each have a hollow structure. The fixed arm 180 and the movable arm 182 have the same sectional shape (strictly speaking, similar shapes). In this case, the section of the fixed arm 180 is larger than the section of the movable arm 182, and a portion of the movable arm 182 resides in the fixed arm 180. That is, the movable arm 182 is nested inside the fixed arm 180. The fixed arm 180 faces the post 114. The movable arm 182 faces the radiation generating unit 120. The fixed arm 180 is connected to the post 114 with the arm hinge portion 116 interposed therebetween and is not movable with respect to the post 114. The movable arm 182 is movable with respect to the fixed arm 180.

The fixed arm 180 is provided with a linear guide rail 151 along which a slide portion 152, to be described below, provided on the movable arm 182 is linearly guided. The linear guide rail 151 is provided on the inner side of the fixed arm 180. The movable arm 182 is provided with the slide portion 152, which slides along the linear guide rail 151. The slide portion 152 is provided on the outer side of the movable arm 182. The slide portion 152 is in engagement with the linear guide rail 151 and is linearly movable along the linear guide rail 151. In the state where the slide portion 152 is in engagement with the linear guide rail 151, the movable arm 182 is supported by the fixed arm 180.

While the slide portion 152 linearly moves back and forth along the linear guide rail 151, the movable arm 182 slidably moves with respect to the fixed arm 180. The extension mechanism may alternatively be a combination of a cam follower and a guide rail, or a combination of a rack and a pinion. The length of stroke of the movable arm 182 is determined by the length of the linear guide rail 151. That is, the length of stroke of the movable arm 182 depends on the length of the linear guide rail 151. Hence, the length of stroke of the movable arm 182 is adjustable by adjusting the length of the linear guide rail 151. For example, if the length of the slide portion 152 is 100 mm and the length of the linear guide rail 151 is 300 mm, the length of stroke of the movable arm 182 is 200 mm, that is, the arm 118 is extendable by 200 mm. If the length of the linear guide rail 151 is 600 mm, the length of stroke of the movable arm 182 is 500 mm, that is, the arm 118 is extendable by 500 mm.

The movable arm 182 is also provided with a slide guide 158, with which the movable arm 182 is positioned. The slide guide 158 is provided on a side of the movable arm 182 that is opposite a side having the slide portion 152 that moves along the linear guide rail 151. The slide guide 158 is provided on the outer side of the movable arm 182, which is nested inside the fixed arm 180. The slide guide 158 of the movable arm 182 always resides inside the fixed arm 180 even if the movable arm 182 is moved.

The slide guide 158 includes a locking member 154 and a compression spring 156. The locking member 154 locks the movement of the movable arm 182 by being in contact with the inner surface of the fixed arm 180. The compression spring 156 presses the locking member 154 against the inner surface of the fixed arm 180. The locking member 154 projects from the body of the slide guide 158. The locking member 154 is made of a material having a high coefficient of static friction, for example, rubber, metal, or the like.

The movable arm 182 is also provided with an unlocking handle 164, with which the locking by the locking member 154 is disabled. The unlocking handle 164 is slidable in the longitudinal direction of the movable arm 182 (a direction of arrow H in FIG. 6). When the locking by the locking member 154 is disabled with the use of the unlocking handle 164, the movable arm 182 becomes movable, that is, the arm 118 becomes extendable and contractible.

Specifically, a pulley 160 and a wire 162 are provided inside the movable arm 182 so that the locking by the locking member 154 is disabled with the use of the unlocking handle 164. The wire 162 is connected to the locking member 154 and the unlocking handle 164 via the pulley 160. A portion of the wire 162 between the unlocking handle 164 and the pulley 160 resides inside the movable arm 182. The wire 162 connected to the unlocking handle 164 stretches in the longitudinal direction of the movable arm 182 and is hooked around the pulley 160, where the wire 162 is redirected. A hole that allows the wire 162 to pass therethrough is provided at a position of the movable arm 182 where the movable arm 182 is in contact with the slide guide 158. The wire 162 is redirected by the pulley 160 orthogonally with respect to the axis of the movable arm 182 and is connected to the locking member 154. Thus, the unlocking handle 164 and the locking member 154 operate in conjunction with each other.

The compression spring 156 presses the locking member 154 against the inner surface of the fixed arm 180. When the unlocking handle 164 is slid toward the radiation generating unit 120 so as to disable the locking, the locking member 154 that has been pressed against the inner surface of the fixed arm 180 is moved away from the inner surface of the fixed arm 180, allowing the arm 118 to freely extend and contract. In this manner, the operator unlocks the movable arm 182 by using the unlocking handle 164. The length of the arm 118 may be set arbitrarily. When the unlocking handle 164 is returned to the initial position, the compression spring 156 presses the locking member 154 against the fixed arm 180, whereby the movable arm 182 is locked, disabling the arm 118 from extending and contracting.

The extendable length of the arm 118 will now be described specifically. The operator often uses a subcompact car or the like in, for example, providing in-home medical services. The trunk of a subcompact car has a width of about 1200 mm. Accordingly, the length of the radiation generating device according to the first embodiment is desired to be 1200 mm or smaller. In the state illustrated in FIG. 1B, the length of the radiation generating device according to the first embodiment is largest from the bottom of the movable portion 110 to the upper end of the post 114 (the upper end of the arm hinge portion 116). Hence, the length from the bottom of the movable portion 110 to the upper end of the post 114 is desired to be about 1200 mm. Suppose that the height of beds installed in intensive-care units (ICU) is in general 1000 mm, a distance SID (see FIGS. 16B and 17) between the focal point of the radiation generating unit 120 and a detecting device that detects radiation is 1000 mm, and the radiation generating unit 120 is positioned at the center of a bed, which has a typical width of 1000 mm. To realize such a situation, the distance from the arm hinge portion 116 to the center of emission from the radiation generating unit 120 needs to be 950 mm or greater. In the state where the radiation generating device is ready to be carried, the radiation generating unit 120 is positioned near the floor 100 so that the center of gravity thereof is lowered. Accordingly, the distance from the arm hinge portion 116 to the end of the radiation generating unit 120 needs to be about 1200 mm. Assuming that the distance from the end of the radiation generating unit 120 to the center of emission from the radiation generating unit 120 is 50 mm, the extendable length of the arm 118 is desired to be about 200 mm.

Figure 7:
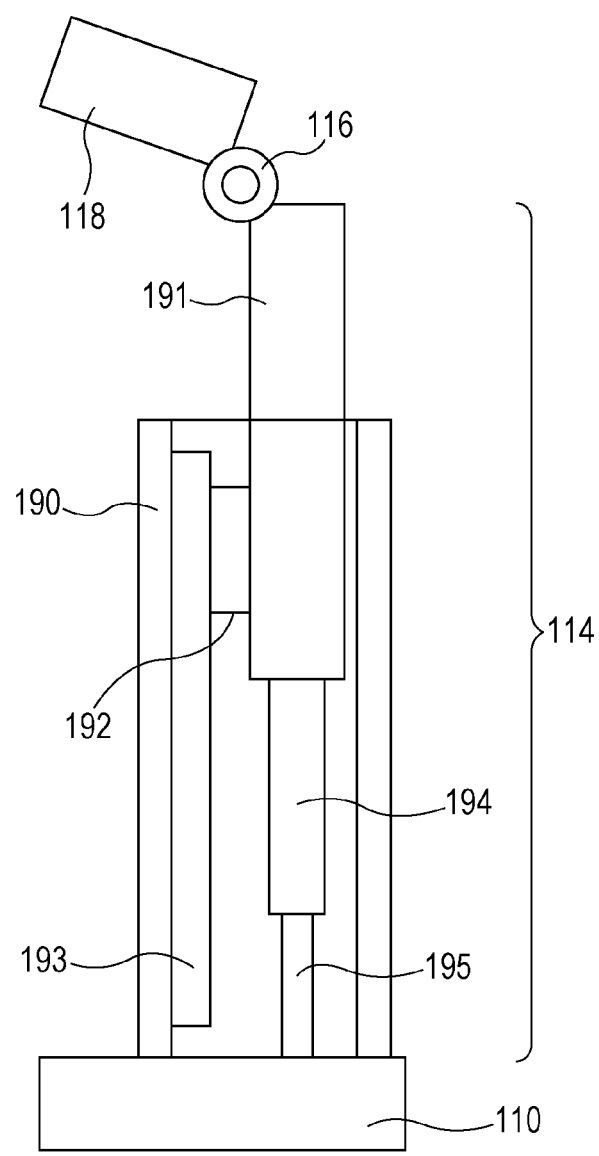
FIG. 7 illustrates an extension mechanism included in a post of the radiation generating device according to the first embodiment.

A specific example of the extension mechanism included in the post 114 will now be described with reference to FIG. 7. The post 114 includes a fixed post 190 and a movable post 191 that is movable with respect to the fixed post 190. The fixed post 190 has a hollow structure. The fixed post 190 and the movable post 191 have the same sectional shape (strictly speaking, similar shapes). The section of the fixed post 190 is larger than the section of the movable post 191. A portion of the movable post 191 resides in the fixed post 190. That is, the movable post 191 is nested inside the fixed post 190.

The fixed post 190 faces the movable portion 110. The movable post 191 faces the arm 118. The fixed post 190 stands vertically on the movable portion 110 and is not movable with respect to the movable portion 110. The movable post 191 is movable with respect to the fixed post 190.

The fixed post 190 is provided with a linear guide rail 193 along which a slide portion 192, to be described below, provided on the movable post 191 is linearly guided. The linear guide rail 193 is provided on the inner side of the fixed post 190. The movable post 191 is provided with the slide portion 192, which slides along the linear guide rail 193. The slide portion 192 is provided on the outer side of the movable post 191. The slide portion 192 is in engagement with the linear guide rail 193 and is linearly movable along the linear guide rail 193. In the state where the slide portion 192 is in engagement with the linear guide rail 193, the movable post 191 is supported by the fixed post 190.

While the slide portion 192 linearly moves along the linear guide rail 193, the movable post 191 slidably moves with respect to the fixed post 190. The extension mechanism may alternatively be a combination of a cam follower and a guide rail, or a combination of a rack and a pinion. The length of stroke of the movable post 191 is determined by the length of the linear guide rail 193. That is, the length of stroke of the movable post 191 depends on the length of the linear guide rail 193. Hence, the length of stroke of the movable post 191 is adjustable by adjusting the length of the linear guide rail 193. For example, if the length of the slide portion 192 is 100 mm and the length of the linear guide rail 193 is 300 mm, the length of stroke of the movable post 191 is 200 mm, that is, the post 114 is extendable by 200 mm. If the length of the linear guide rail 193 is 600 mm, the length of stroke of the movable post 191 is 500 mm, that is, the post 114 is extendable by 500 mm.

The fixed post 190 houses a compression mechanism 194 and a supporting member 195 that is connected to a portion of the fixed post 190. The compression mechanism 194 is connected to the supporting member 195 and the movable post 191. The extendable length of the arm 118 that is allowed by the extension mechanism included in the arm 118 and the extendable length of the post 114 that is allowed by the extension mechanism included in the post 114 may be the same as each other.

If the extendable length of the post 114 is large, a gas spring may be used as the compression mechanism 194. Alternatively, the compression mechanism 194 may be a spring or the like. The force exerted by the compression mechanism 194 may be set to a value corresponding to the total weight of the movable post 191, the radiation generating unit 120, and the elements provided between the two. Thus, the post 114 is extendable and contractible with a small force.

The mechanism of locking the extension and contraction of the arm 118 may be applied to the mechanism of locking the extension and contraction of the post 114. If the compression mechanism 194 is a gas spring, the gas spring may be capable of locking the post 114 that has been extended or contracted by any length.

Figure 8A:
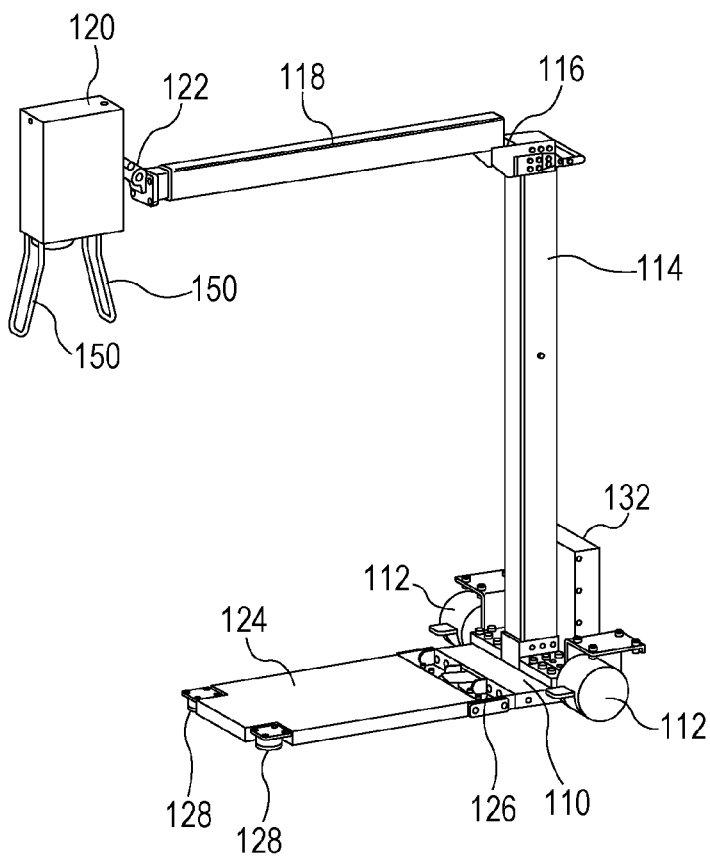
FIGS. 8A and 8B illustrate the radiation generating device in exemplary states of extension and contraction, respectively, according to the first embodiment.
Figure 8B:
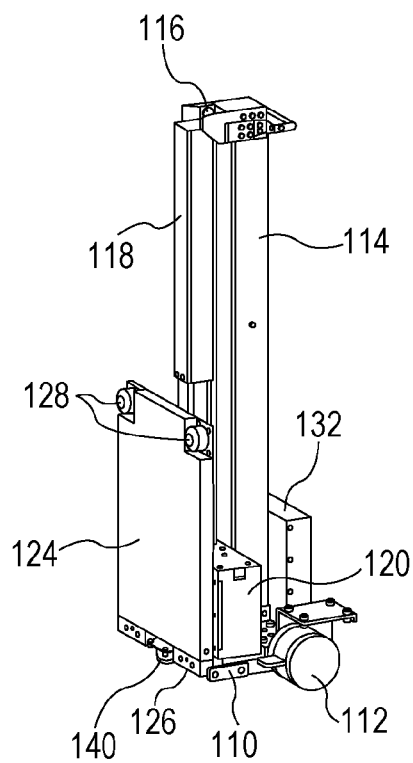
Figure 9A:
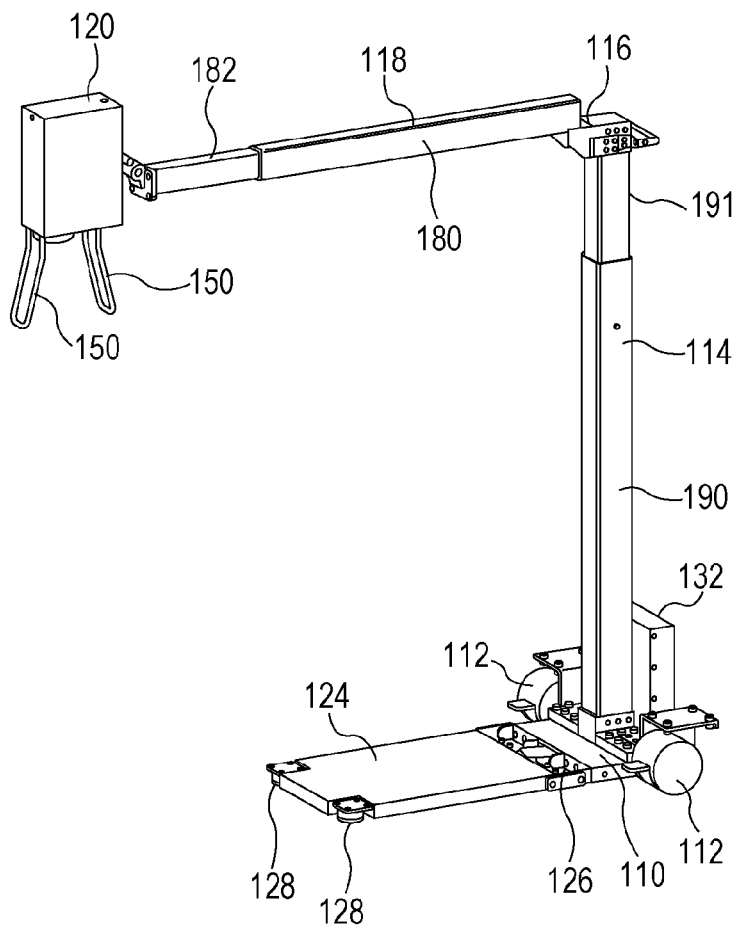
FIGS. 9A and 9B illustrate the radiation generating device in another exemplary state of extension and contraction, respectively, according to the first embodiment.
Figure 9B:
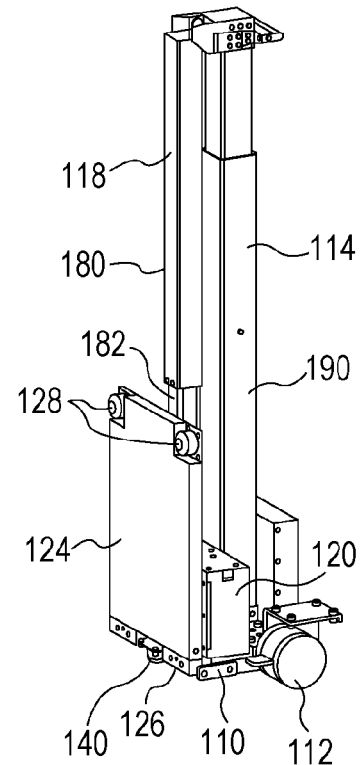

Forms of extension and contraction of the radiation generating device according to the first embodiment of the present invention will now be described with reference to FIGS. 8A, 8B, 9A, and 9B. FIGS. 8A and 8B illustrate a form of the radiation generating device with the arm 118 and the post 114 each being in the shortest state. FIGS. 9A and 9B illustrate another form of the radiation generating device with the arm 118 and the post 114 each being in the longest state. FIGS. 8A and 9A are front perspective views of the radiation generating device that is ready for imaging. FIGS. 8B and 9B are front perspective views of the radiation generating device that is ready to be carried.

The length of the post 114 is set in accordance with the length of the arm 118 and the length of the radiation generating unit 120 and such that the arm 118 is allowed to be tucked away together with the radiation generating unit 120. When the arm 118 is in the shortest state as illustrated in FIG. 8A, the arm 118 is allowed to be tucked away together with the radiation generating unit 120 by being closed as illustrated in FIG. 8B, regardless of the length of the post 114. The extendable lengths allowed by the extension mechanism included in the arm 118 illustrated in FIG. 6 and the extension mechanism included in the post 114 illustrated in FIG. 7 are set such that the arm 118 is allowed to be tucked away together with the radiation generating unit 120.

Specifically, the length of the post 114 in the shortest state is set in accordance with the length of the arm 118 in the shortest state and the length of the radiation generating unit 120 and such that the arm 118 is allowed to be tucked away together with the radiation generating unit 120. More specifically, the length of the post 114 in the shortest state is larger than the sum of the length of the arm 118 in the shortest state and the length of the radiation generating unit 120. Hence, the arm 118 in the shortest state is allowed to be tucked away together with the radiation generating unit 120 even if the post 114 is in the shortest state.

The length of the post 114 in the longest state is set in accordance with the length of the arm 118 in the longest state and the length of the radiation generating unit 120 and such that the arm 118 is allowed to be tucked away together with the radiation generating unit 120. More specifically, the length of the post 114 in the longest state is larger than the sum of the length of the arm 118 in the longest state and the length of the radiation generating unit 120. Hence, the arm 118 in the longest state is allowed to be tucked away together with the radiation generating unit 120.

How the arm 118 and the radiation generating unit 120 are tucked away will now be described with reference to FIGS. 10A and 10B. Referring to FIG. 10A, to carry the radiation generating device, the operator closes the arm 118 such that the arm 118 is tucked away together with the radiation generating unit 120. Subsequently, the operator closes the supporting foot portion 124 such that the supporting foot portion 124 stands vertically.

Referring to FIG. 10B, in the state where the arm 118 and the radiation generating unit 120 are tucked away, a position H1 of the supporting foot portion 124 is higher than a position H2 of the radiation generating unit 120. The position H1 of the supporting foot portion 124 corresponds to the upper end (a face at the highest position) of the supporting foot portion 124. The position H2 of the radiation generating unit 120 corresponds to the upper end (a face at the highest position) of the radiation generating unit 120.

Specifically, the extendable lengths of the arm 118 and the post 114 are adjusted such that the position H1 of the supporting foot portion 124 is higher than the position H2 of the radiation generating unit 120. Alternatively, the length of the supporting foot portion 124 may be adjusted. Thus, the supporting foot portion 124 covers and protects the radiation generating unit 120.

The supporting foot portion 124 may also cover the rotational portion 122 including the swivel hinge 123 and the tilt hinge 125 (see FIG. 3). This is because the rotational portion 122 tends to have relatively low strength and to be fragile to external forces. Hence, the position H1 of the supporting foot portion 124 may be higher than a position H3 of the rotational portion 122. The position H3 of the rotational portion 122 corresponds to the upper end (a face at the highest position) of the rotational portion 122. If the rotational portion 122 is resistant to external forces, it is only necessary that the position H1 of the supporting foot portion 124 is higher than the position H2 of the radiation generating unit 120.

As described above, according to the first embodiment of the present invention, the radiation generating device includes the arm 118 configured to support the radiation generating unit 120 that generates radiation, and the post 114 configured to support the arm 118. The radiation generating device further includes the movable portion 110 configured to support the post 114 and to allow the radiation generating device to move on the floor 100, and the supporting foot portion 124 that is rotatable in such a manner as to be opened and closed with respect to the movable portion 110.

The first embodiment of the present invention also provides a radiation imaging apparatus (not illustrated) that includes the radiation generating device, a detecting device configured to detect the radiation that has been generated by the radiation generating device and has been transmitted through a subject and to output data on an image corresponding to the radiation, and a display device that displays the image. Examples of the radiation include not only beams as particles (including photons) such as α-rays, β-rays, γ-rays, X-rays, and the like that are emitted as a result of radioactive decay, but also beams such as corpuscular rays and cosmic rays that have energy substantially the same as or higher than the energy of the foregoing beams.

According to the first embodiment of the present invention, the supporting foot portion 124 included in the radiation imaging apparatus is a plate-like member but is not limited thereto. The supporting foot portion 124 only needs to have a predetermined rigidity and to be openable and closable with respect to the movable portion 110. For example, the supporting foot portion 124 may be any of the following: a plurality of bar-like members, a meshed member, a member having a curved surface, and so forth. According to the first embodiment of the present invention, the arm 118 and the post 114 included in the radiation imaging apparatus are separate members. Alternatively, the arm 118 and the post 114 may be combined into one integral element having a function as the arm 118 and a function as the post 114. Such an element is configured to connect the radiation generating unit 120 and the movable portion 110 to each other and to support the radiation generating unit 120. For example, the element may be a member that has a bellows structure with a predetermined rigidity and is foldable such that the radiation generating unit 120 is allowed to be tucked away.

Second Embodiment

A radiation imaging apparatus according to a second embodiment of the present invention will now be described. The second embodiment concerns an X-ray imaging apparatus that emits X-rays, i.e., radioactive rays of a typical type.

The use of movable X-ray imaging apparatuses that are capable of X-ray imaging not only in imaging rooms but also in patients' rooms and operating rooms has been increasing particularly in medical scenes occurring at disaster sites and in in-home services. Such a movable X-ray imaging apparatus includes a movable cart portion, on which an X-ray tube configured to emit X-rays toward a subject and an X-ray controlling unit are mounted. Some recent movable X-ray imaging apparatuses include monitors that immediately display images that have been taken.

In recent years, there have been increasing demands for diagnosis with X-ray images in various medical scenes occurring in in-home services, in nursing homes, at disaster sites, and so forth. Accordingly, there have been increasing demands for portable X-ray imaging apparatuses that are more portable than the above known movable X-ray imaging apparatuses and that can be carried to the outside of hospitals.

Known portable X-ray imaging apparatuses each include an X-ray tube and a supporting member configured to support the X-ray tube that are either combined into an integral body or provided as separate bodies. In many cases, such an X-ray imaging apparatus is foldable for increased portability. In some other cases, the X-ray imaging apparatus includes separable elements that can be assembled, out of consideration for higher portability. Hence, to take images on site, the apparatus needs to be unfolded or assembled after being carried to the site. In addition, the position of the X-ray tube needs to be adjusted in accordance with the position of the subject and the site of the subject that is to be imaged. The unfolding/assembling work and the adjusting work may occupy a large part of working time that is spent for X-ray imaging especially in cases where imaging is performed at several sites per day in providing in-home services and visits to nursing homes. In such situations, the improvement of working efficiency may be hindered.

To solve the above problem, different radiation imaging apparatuses are disclosed by Japanese Patent Laid-Open No. 2012-65947 and Japanese Patent Laid-Open No. 2010-57546. In the apparatus disclosed by Japanese Patent Laid-Open No. 2012-65947, a supporting member that supports an X-ray tube is provided with marks, such as lamps, representing sites to be imaged. The worker or the operator can set the X-ray tube at the best position by simply positioning the X-ray tube with reference to the marks without making fine adjustment. Consequently, working efficiency is increased. In the apparatus disclosed by Japanese Patent Laid-Open No. 2010-57546, a supporting member that supports an X-ray tube has a stepladder-like structure. Therefore, the apparatus is installable by spreading supporting legs, and the height of the X-ray tube is adjustable by adjusting the angle between the supporting legs.

Portable X-ray imaging apparatuses are desired to be installable in various medical scenes occurring in in-home services, in nursing homes, at disaster sites, and so forth. In in-home services and nursing homes, X-ray imaging apparatuses are desired to be easy to carry and easy to assemble so as to be quickly installable on site by a limited number of workers, usually, one or two. At disaster sites, imaging is often performed in temporary facilities constructed outdoor on rough terrains. Therefore, X-ray imaging apparatuses are desired to be so operable as to be installed and positioned quickly and accurately regardless of the environment.

Hence, in the second embodiment, a portable X-ray imaging apparatus that is superior in usability, handleability, and so forth and exhibits increased operability and working efficiency will be described.

Figure 11:
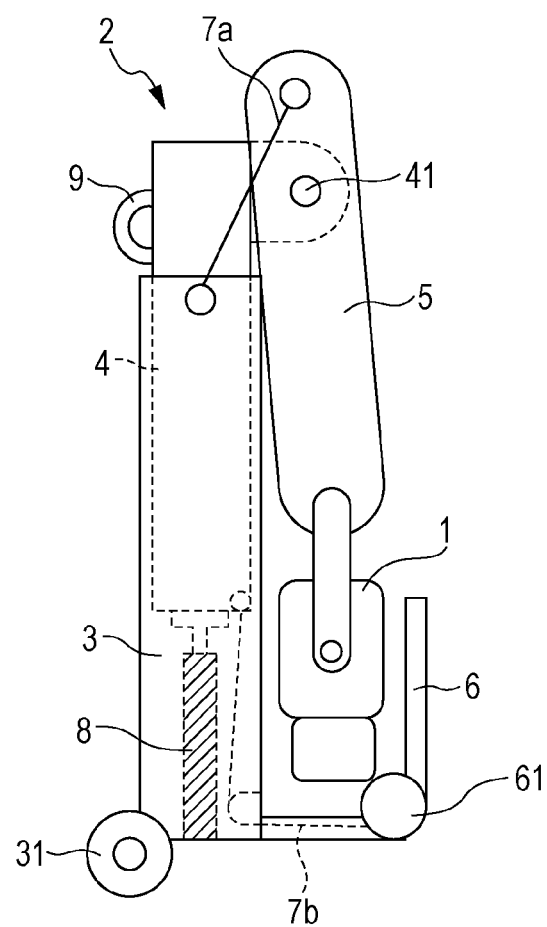
FIG. 11 illustrates a configuration of an X-ray imaging apparatus as a radiation imaging apparatus according to a second embodiment of the present invention.
Figure 12:
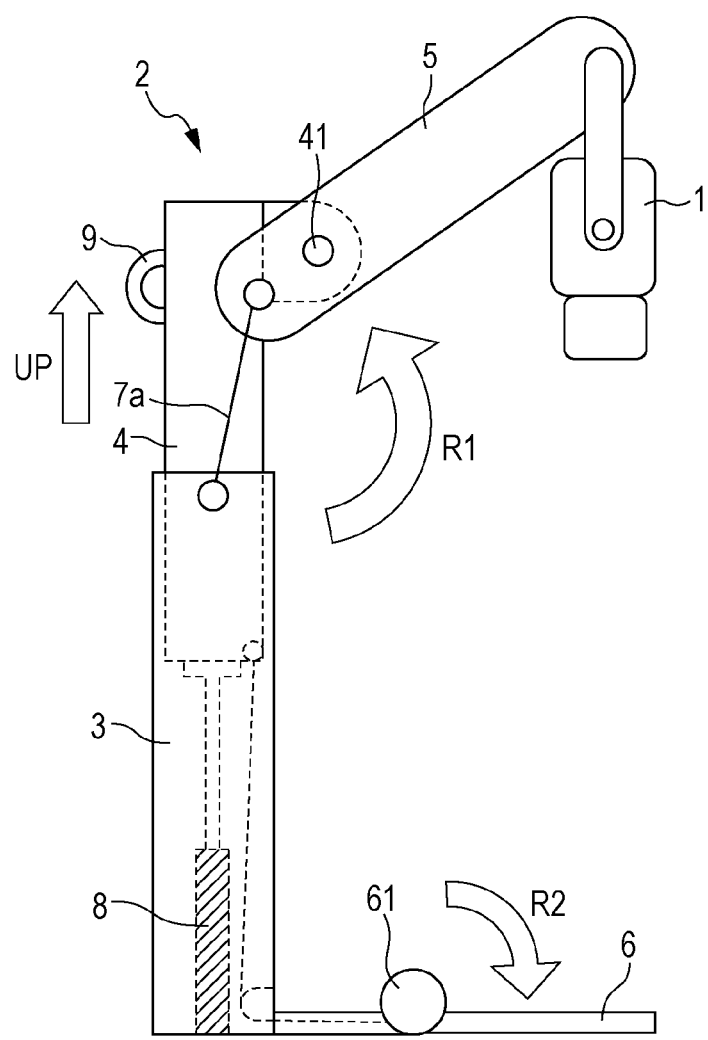
FIG. 12 illustrates the X-ray imaging apparatus according to the second embodiment in an exemplary extended or expanded state.

FIG. 11 illustrates a configuration of the portable X-ray imaging apparatus according to the second embodiment of the present invention. FIG. 12 illustrates how the portable X-ray imaging apparatus according to the second embodiment moves. Note that the portable X-ray imaging apparatus according to the second embodiment includes a detecting device (not illustrated) configured to detect radiation that has been transmitted through a subject and to output data on an image corresponding to the radiation, and a display device (not illustrated) configured to display the image. Referring to FIGS. 11 and 12, an X-ray tube 1 (corresponding to the radiation generating unit 120 according to the first embodiment) is configured to emit X-rays. A holding mechanism 2 is configured to hold the X-ray tube 1 both in a state where the X-ray imaging apparatus is ready to be carried and in a state where the X-ray imaging apparatus is ready for imaging. The holding mechanism 2 includes an extension mechanism and a rotational mechanism so as to provide portability. The holding mechanism 2 is connected to the X-ray tube 1 but may be removable from the X-ray tube 1, considering the ease of assembly and maintenance. A post base portion 3 is one of post elements included in the holding mechanism 2 and bears the weight of the holding mechanism 2 that stands vertically. The post base portion 3 may be provided with wheels 31 for increased portability of the apparatus.

A post movable portion 4 is another post element included in the holding mechanism 2 and is connected to and is nested inside the post base portion 3. The post base portion 3 and the post movable portion 4 in combination function as a post (corresponding to the post 114 according to the first embodiment) of the apparatus. In the state where the apparatus is ready to be carried, the post movable portion 4 is tucked away in the post base portion 3 so that the size of the apparatus as a whole is reduced and the portability is increased. To perform imaging, the post movable portion 4 is lifted and is made to project from the post base portion 3. In this manner, the post movable portion 4 is movable such that the X-ray tube 1 reaches a desired imaging position. An arm 5 (corresponding to the arm 118 according to the first embodiment) is one of the elements included in the holding mechanism 2 and is connected to the X-ray tube 1 at one longitudinal end thereof and to the upper end of the post movable portion 4 at the other longitudinal end thereof with the aid of a movable joint 41. To carry or put away the apparatus, the arm 5 is rotated about the movable joint 41 so that the size of the apparatus as a whole is reduced and the portability is increased. To use the apparatus, that is, to perform imaging, the post movable portion 4 is lifted (as illustrated by arrow UP in FIG. 12). Simultaneously, the arm 5 is rotated upward about the movable joint 41 (as illustrated by arrow R1 in FIG. 12), whereby the X-ray tube 1 is moved to a desired imaging position. Thus, the apparatus becomes ready for imaging.

A supporting foot 6 is connected to the lower end of the post base portion 3. The supporting foot 6 has a joint 61. The supporting foot 6 is rotatable about the joint 61 in such a manner as to cover the X-ray tube 1, whereby the size of the apparatus as a whole is reduced and the portability is increased when the apparatus is put away or carried. To perform imaging, while the post movable portion 4 is lifted, the supporting foot 6 is rotated about the joint 61 and is thus opened (as illustrated by arrow R2 in FIG. 12), whereby the weight of the apparatus is supported so that the apparatus can stand by itself.

A link mechanism 7a includes a wire or the like and is connected to a position of the arm 5 that is near the movable joint 41 at one end thereof and to the post base portion 3 at the other end thereof. When the post movable portion 4 is lifted, the arm 5 receives a tensile force from the link mechanism 7a and rotates about the movable joint 41, where the arm 5 is connected to the post movable portion 4. Consequently, as illustrated in FIG. 12, the X-ray tube 1 is lifted to a position where imaging is to be performed. As with the link mechanism 7a, a link mechanism 7b includes a wire or the like and is connected to the joint 61 of the supporting foot 6 at one end thereof and to the post movable portion 4 at the other end thereof. When the post movable portion 4 is lifted, the joint 61 receives a tensile force from the link mechanism 7b and rotates, whereby the supporting foot 6 is rotated about the joint 61. Consequently, as illustrated in FIG. 12, the supporting foot 6 is opened and supports the weight of the apparatus so that the apparatus can stand by itself. Since the lifting and positioning of the X-ray tube 1 and the opening and positioning of the supporting foot 6 are performed simultaneously as described above, the working efficiency in setting the X-ray imaging apparatus is increased.

An assist mechanism 8 assists the lifting of the post movable portion 4 and includes any of the following: a spring such as a gas spring, a coil spring, a conston spring, or a spiral spring; an actuator such as an electrical motor; or a jack such as a hydraulic jack. The assist mechanism 8 is provided between the post base portion 3 and the post movable portion 4. The assist mechanism 8 exerts a spring force or a driving force in an upward direction against the direction in which the weight of the post movable portion 4 acts. Therefore, the total weight of the post movable portion 4, the arm 5, and the X-ray tube 1 that is to be borne by the worker or the operator when the post movable portion 4 is lifted is reduced, whereby the working efficiency in the lifting operation is increased. A grip member 9, such as a handle or a recess, is provided on the post movable portion 4. The worker grips the grip member 9 in lifting the post movable portion 4.

Figure 13:
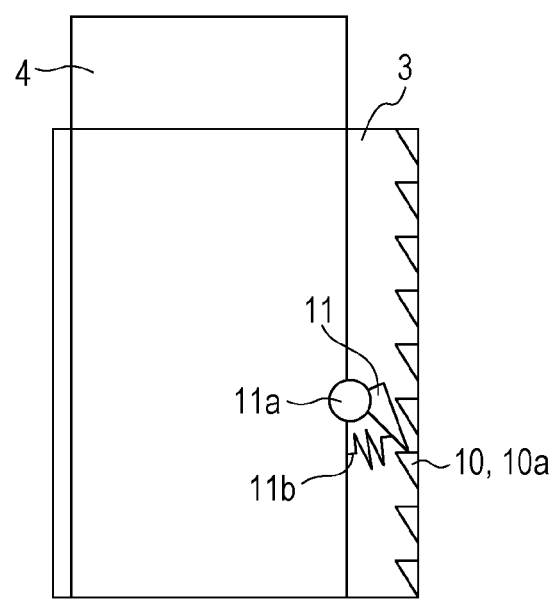
FIG. 13 illustrates the X-ray imaging apparatus according to the second embodiment.

FIG. 13 illustrates a mechanism included in the portable X-ray imaging apparatus according to the second embodiment of the present invention. After the X-ray tube 1 has been moved to a desired imaging position with the lifting of the post movable portion 4, the mechanism illustrated in FIG. 13 retains the position of the lifted post movable portion 4 while preventing the post movable portion 4 from being lowered. As illustrated in FIG. 13, a latch receiving mechanism 10 is provided on the inner side of the post base portion 3. The latch receiving mechanism 10 includes a plurality of projections 10a that are linearly arranged in the longitudinal direction of the post movable portion 4. The latch receiving mechanism 10 may include a plurality of grooves instead of the projections 10a. A movable latch pin 11 is oriented in the longitudinal direction of the post movable portion 4 and includes a rotating shaft 11a and a spring member 11b. The movable latch pin 11 is rotatable about the rotating shaft 11a, while the spring member 11b forcibly keeps the tip of the movable latch pin 11 away from the post movable portion 4. In this state, the latch receiving mechanism 10 and the movable latch pin 11 face each other and are in contact with each other inside the post base portion 3.

When the post movable portion 4 is lifted, the following occurs:

(i) the tip of the movable latch pin 11 comes into contact with one of the projections 10a of the latch receiving mechanism 10 that resides immediately above the movable latch pin 11;

(ii) as the post movable portion 4 is further forcibly lifted, the tip of the movable latch pin 11 is forcibly pushed up; and (iii) the movable latch pin 11 goes over the projection 10a residing immediately thereabove and engages with that projection 10a.

The post movable portion 4 continues to be lifted while the movable latch pin 11 repeatedly makes the above series of movements (i) to (iii). When the lifting of the post movable portion 4 is stopped, the post movable portion 4 is lowered under its own weight. However, since the spring member 11b forcibly keeps the tip of the movable latch pin 11 away from the post movable portion 4, the movable latch pin 11 engages with the latch receiving mechanism 10, whereby the lowering of the post movable portion 4 is stopped. The movable latch pin 11 is operable from the outside such that the movable latch pin 11 that has been in engagement with the latch receiving mechanism 10 is disengaged from the latch receiving mechanism 10. Hence, to lower the post movable portion 4 at the worker's discretion, the worker disengages the movable latch pin 11 from the latch receiving mechanism 10.

Third Embodiment

Figure 14A:
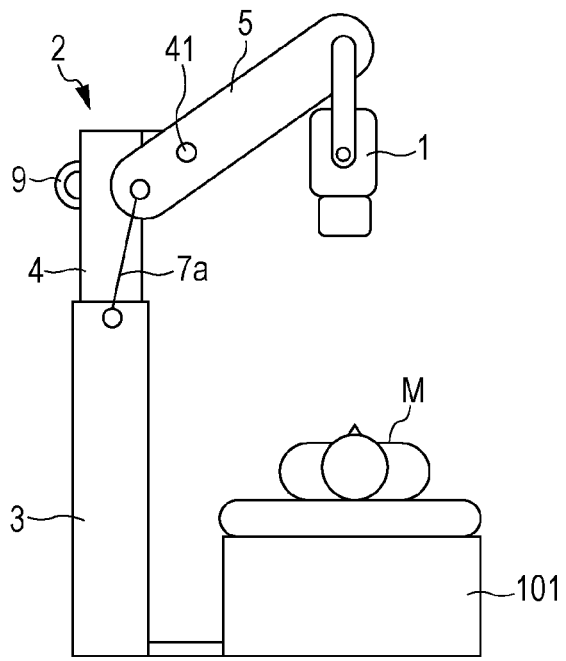
FIGS. 14A to 14C illustrate an X-ray imaging apparatus according to a third embodiment of the present invention.
Figure 14B:
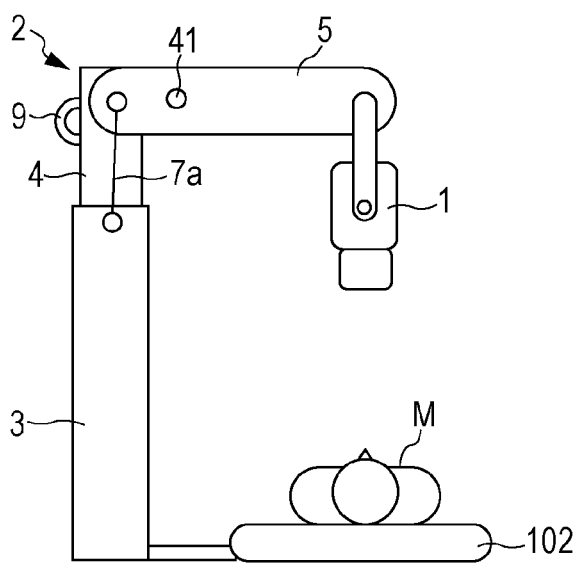
Figure 14C:
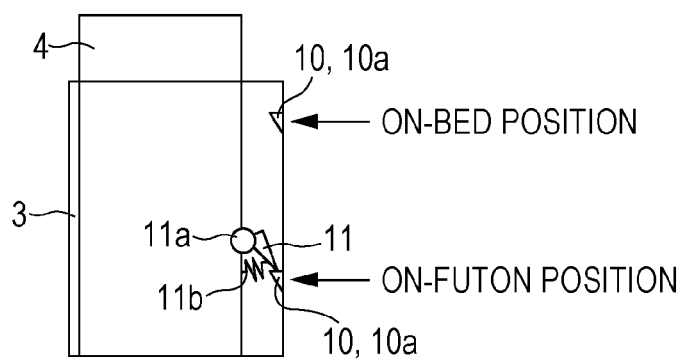

FIGS. 14A and 14B illustrate different imaging states of a portable X-ray imaging apparatus according to a third embodiment of the present invention. In the following description, elements that are substantially the same as or correspond to those described in the second embodiment are denoted by corresponding ones of the reference numerals that are used in the second embodiment. The third embodiment is obtained by making a change to the second embodiment, specifically, by simplifying the work of adjusting the position of the X-ray tube 1. Thus, the scope of the present invention is widened. FIG. 14A illustrates the portable X-ray imaging apparatus that is in a state where a subject M lying on a bed 101 is to be imaged. FIG. 14B illustrates the portable X-ray imaging apparatus that is in a state where the subject M lying on a futon 102 is to be imaged. FIG. 14C illustrates the arrangement of projections 10a included in a latch receiving mechanism 10 according to the third embodiment.

As illustrated in FIGS. 14A and 14B, to take images with the portable X-ray imaging apparatus, the position of the X-ray tube 1 needs to be adjusted in accordance with the position and posture of the subject M. Such an adjustment work hinders the improvement of the working efficiency in the imaging operation. Accordingly, as illustrated in FIG. 14C, the projections 10a of the latch receiving mechanism 10 are provided only at predetermined positions corresponding to positions of the X-ray tube 1 that are expected to be taken in the imaging operation, for example, at an "on-bed position" and an "on-futon position". Thus, the worker can instantly determine the position of the X-ray tube 1 without spending extra time for the positioning work. Consequently, the working efficiency in the imaging operation is increased. The positions of the subject M include not only lying positions but also any other positions that are to be taken in X-ray imaging, such as a sitting position, a half-sitting position, and a standing position.

Fourth Embodiment

Figure 15:
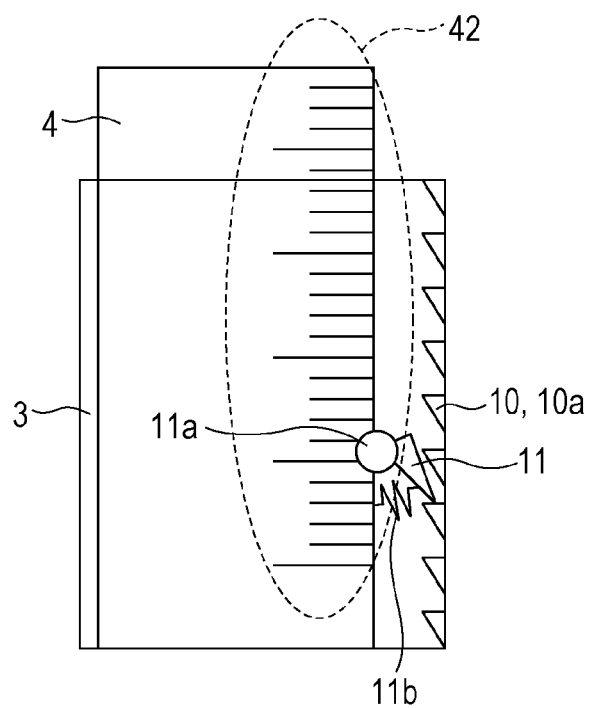
FIG. 15 illustrates an X-ray imaging apparatus according to a fourth embodiment of the present invention.

FIG. 15 illustrates a mechanism included in a portable X-ray imaging apparatus according to a fourth embodiment of the present invention. The fourth embodiment is obtained by making a change to the third embodiment, specifically, to the mechanism of simplifying the work of adjusting the position of the X-ray tube 1. The fourth embodiment employs a mechanism in which the position of the X-ray tube 1 is adjusted with reference to a scale, instead of or in addition to the mechanism employed in the third embodiment. Thus, the scope of the present invention is widened.

To increase the working efficiency in the positioning of the X-ray tube 1 described in the third embodiment, a scale 42 may be provided on the post movable portion 4. If the scale 42 is provided on the post movable portion 4 in advance and is referred to when the position of the X-ray tube 1 is adjusted in accordance with the position and posture of the subject M, the worker can finish the adjustment work by simply moving the post movable portion 4 with reference to the scale 42.

Fifth Embodiment

FIGS. 16A to 16D illustrate a portable X-ray imaging apparatus according to a fifth embodiment of the present invention. The fifth embodiment is obtained by making a change to the third and fourth embodiments, specifically, to the mechanism of simplifying the work of adjusting the position of the X-ray tube 1. In the fifth embodiment, the X-ray tube 1 is positioned with reference to the position of an X-ray-image detector, instead of using the mechanisms employed in the third and fourth embodiments. Thus, the scope of the present invention is widened.

Figure 16A:
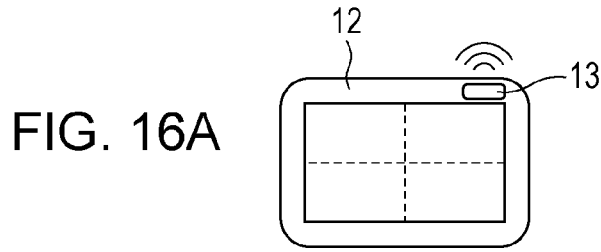
FIGS. 16A to 16D illustrate an X-ray imaging apparatus that includes an X-ray-image detector according to a fifth embodiment of the present invention.
Figure 16B:
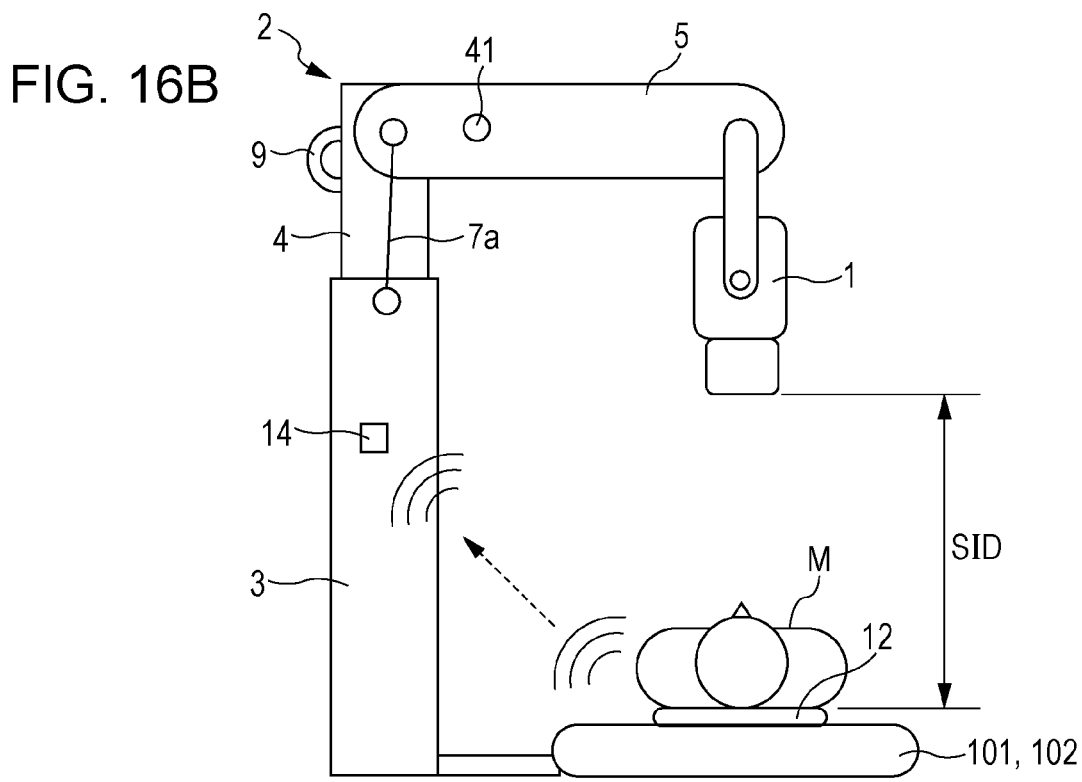

FIG. 16A illustrates an X-ray-image detector 12 to be used when the subject M is imaged. FIG. 16B illustrates a system of the portable X-ray imaging apparatus according to the fifth embodiment.

The X-ray-image detector 12 illustrated in FIG. 16A detects the X-rays that have been emitted from the X-ray tube 1 toward the subject M and have been transmitted through the subject M, and converts the detected X-rays into an image. The X-ray-image detector 12 includes a position information transmitter 13 that transmits information on the position of the X-ray-image detector 12. The holding mechanism 2 illustrated in FIG. 16B is provided with a position information receiver 14 that receives a signal transmitted from the position information transmitter 13. When the X-ray-image detector 12 is set below a site of the subject M that is to be imaged, the position information transmitter 13 transmits information on the position of the X-ray-image detector 12 to the position information receiver 14. The position information receiver 14, which is provided at a position of the holding mechanism 2 that is near the subject M, receives the information on the position of the X-ray-image detector 12 by means of wired or wireless communication. In accordance with the information received from the X-ray-image detector 12, the lifting of the post movable portion 4 is stopped when the X-ray tube 1 has reached a position at a predetermined optimum distance (imaging distance) SID from the X-ray-image detector 12.

Figure 16C:
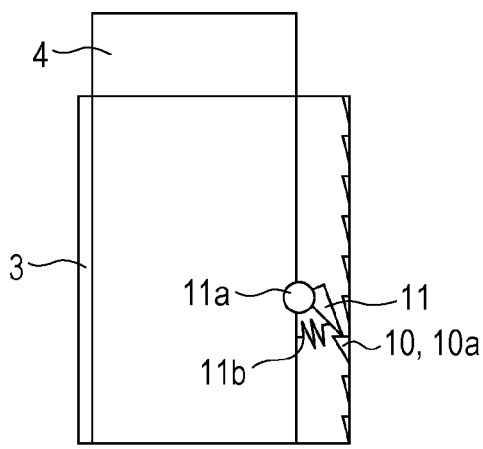
Figure 16D:
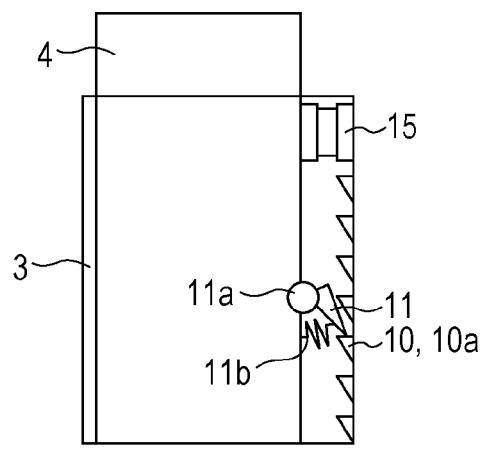

FIGS. 16C and 16D illustrate stopping mechanisms, respectively, each configured to stop the post movable portion 4. The stopping mechanisms each include the movable latch pin 11. When the post movable portion 4 has been lifted to such a position that the X-ray tube 1 and the X-ray-image detector 12 are at the optimum imaging distance SID from each other, the movable latch pin 11 is fixed. Since the tip of the movable latch pin 11 is not forcibly pressed down even if it comes into contact with one of the projections 10a of the latch receiving mechanism 10 that resides immediately thereabove, the movable latch pin 11 does not goes over that projection 10a residing immediately thereabove. Thus, the post movable portion 4 is stopped at the intended position. Alternatively, as illustrated in FIG. 16C, only a predetermined one of the projections 10a of the latch receiving mechanism 10 may be allowed to engage with the movable latch pin 11 while the other projections 10a are retracted. In such a case, the post movable portion 4 stops only at the predetermined position, that is, the post movable portion 4 can be stopped as intended.

As another alternative, referring to FIG. 16D, a braking member 15 may be provided between the post base portion 3 and the post movable portion 4. When the post movable portion 4 has been lifted to such a position that the X-ray tube 1 and the X-ray-image detector 12 are at the optimum imaging distance SID from each other, the braking member 15 is activated and stops the post movable portion 4.

Thus, the worker can instantly determine the position of the X-ray tube 1 without spending extra time for the positioning work. Consequently, the working efficiency in the imaging operation is increased.

Sixth Embodiment

Figure 17:
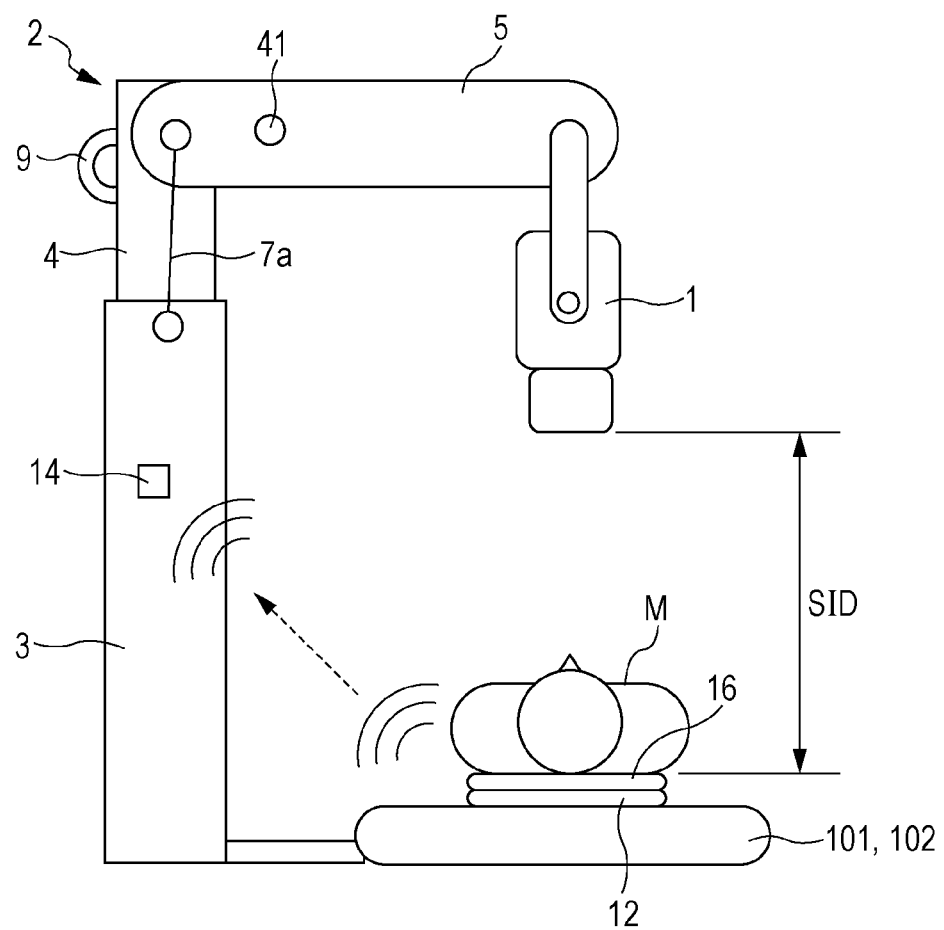
FIG. 17 illustrates an X-ray imaging apparatus according to a sixth embodiment of the present invention that includes a grid.

FIG. 17 illustrates a portable X-ray imaging apparatus according to a sixth embodiment of the present invention. The sixth embodiment is obtained by making a change to the fifth embodiment, specifically, to the mechanism of simplifying the work of adjusting the position of the X-ray tube 1. In the sixth embodiment, the X-ray tube 1 is positioned with reference to the position of a grid 16, instead of using the mechanism employed in the fifth embodiment. Thus, the scope of the present invention is widened. Referring to FIG. 17, the grid 16 removes scattered rays that are derived when the X-rays having been emitted from the X-ray tube 1 are transmitted through the subject M. To perform X-ray imaging, the grid 16 is superposed on the X-ray-image detector 12. The position information transmitter 13 may alternatively be provided on the grid 16. When the grid 16 and the X-ray-image detector 12 are set below a site of the subject M that is to be imaged, the position information transmitter 13 transmits information on the position of the grid 16 to the position information receiver 14 provided at a position of the holding mechanism 2 that is near the subject M. Thus, the position information receiver 14 receives the information on the position of the grid 16.

As in the fifth embodiment, in accordance with the information on the position of the grid 16, the lifting of the post movable portion 4 is stopped when the X-ray tube 1 has reached such a position that the distance between the X-ray tube 1 and the grid 16 corresponds to a focal length that is most suitable for imaging. The mechanism of stopping the post movable portion 4 may be the same as that employed in the fourth embodiment.

Seventh Embodiment

Figure 18:
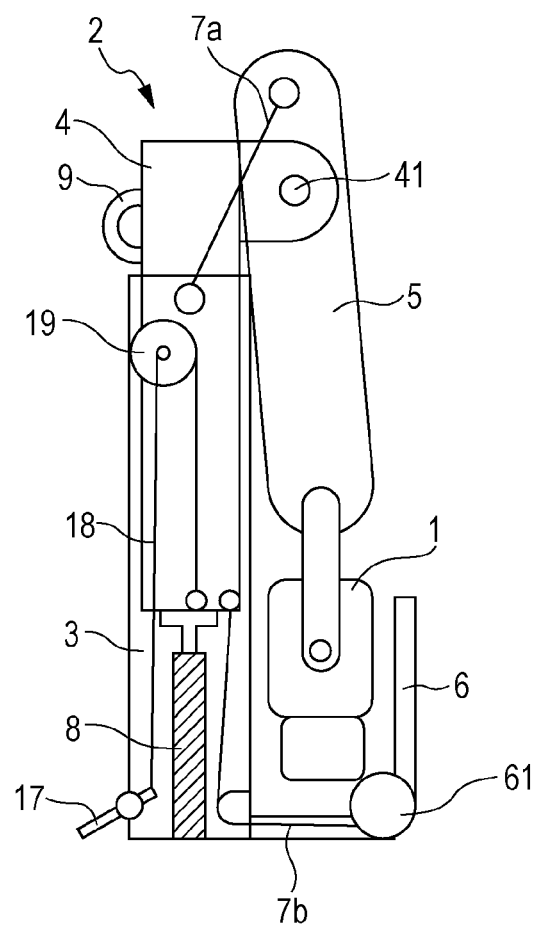
FIG. 18 illustrates an X-ray imaging apparatus in a collapsed state according to a seventh embodiment of the present invention.

FIG. 18 illustrates a portable X-ray imaging apparatus according to a seventh embodiment of the present invention. The seventh embodiment is obtained by making a change to the second embodiment. Specifically, the X-ray tube 1 is positioned by using a pedal 17 operated by foot, instead of using hands as described in the second embodiment. Thus, the scope of the present invention is widened.

Referring to FIG. 18, the pedal 17 (pedal mechanism) is provided at the bottom of the holding mechanism 2. To lift the post movable portion 4, the worker may step on the pedal 17 instead of gripping the grip member 9. A pull-type link member 18 includes a wire or the like and is connected to the pedal 17 at one end thereof and to the post movable portion 4 at the other end thereof. A pulley 19 is provided at a position of the post base portion 3 that is above the points where the pull-type link member 18 is connected to the pedal 17 and the post movable portion 4. The pull-type link member 18 stretches upward from the pedal 17 provided on the lower side, is hooked around the pulley 19 provided on the upper side, and is connected to a position of the post movable portion 4 that is below the pulley 19.

When the worker steps on the pedal 17, the pull-type link member 18 is pulled down toward the pedal 17, whereby the pull-type link member 18 pulls up the post movable portion 4 with the aid of the pulley 19. If the length of lifting of the post movable portion 4 that is realized only by stepping on the pedal 17 is insufficient, the pulley 19 may include two pulleys so that the post movable portion 4 can be lifted by a satisfactory length.

Eighth Embodiment

Figure 19:
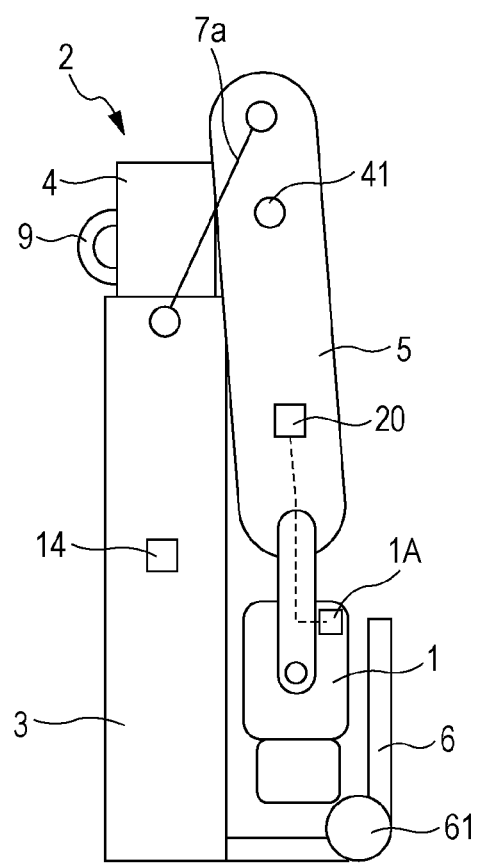
FIG. 19 illustrates an X-ray imaging apparatus according to an eighth embodiment of the present invention.

FIG. 19 illustrates a portable X-ray imaging apparatus according to an eighth embodiment of the present invention. The eighth embodiment is obtained by making a change to the second embodiment, specifically, by adding a function of preventing accidental emission of radiation from the X-ray tube 1 in conjunction with the positioning of the X-ray tube 1. Thus, the scope of the present invention is widened.

Referring to FIG. 19, a position detecting sensor 20 is provided on the holding mechanism 2. The position detecting sensor 20 senses and detects the shape of the holding mechanism 2 or the position of the X-ray tube 1. The position detecting sensor 20 is connected to a power supply unit 1A of the X-ray tube 1. In a state where the X-ray tube 1 is at a tucked position, the X-ray tube 1 receives a signal from the position detecting sensor 20 and the power supply unit 1A is automatically turned off. Thus, accidental emission of radiation from the X-ray tube 1 due to a malfunction of an emission switch is prevented, and safety is provided.

The position detecting sensor 20 may detect the shape of the holding mechanism 2 by detecting the position of the post movable portion 4 or by detecting the angle of the arm 5. The position detecting sensor 20 may be an infrared laser, or a rotary encoder provided between the post movable portion 4 and the arm 5. The position detecting sensor 20 may be provided on the X-ray tube 1 instead of the holding mechanism 2.

Ninth Embodiment

A ninth embodiment of the present invention is obtained by making a change to the second embodiment, specifically, by adding a function of inputting power to the X-ray tube 1 in conjunction with the work of positioning the X-ray tube 1. Thus, the scope of the present invention is widened.

As in the eighth embodiment, the position detecting sensor 20 that detects the shape of the holding mechanism 2 or the position of the X-ray tube 1 is provided on the holding mechanism 2. The position detecting sensor 20 is connected to the power supply unit 1A of the X-ray tube 1. When the post movable portion 4 is lifted and the X-ray tube 1 has been moved from the tucked position to the imaging position, the X-ray tube 1 receives a signal from the position detecting sensor 20 and the power supply unit 1A is automatically turned on. Since the worker can skip a step of inputting power to the X-ray tube 1, the working efficiency in the X-ray imaging operation is increased.

Tenth Embodiment

Figure 20:
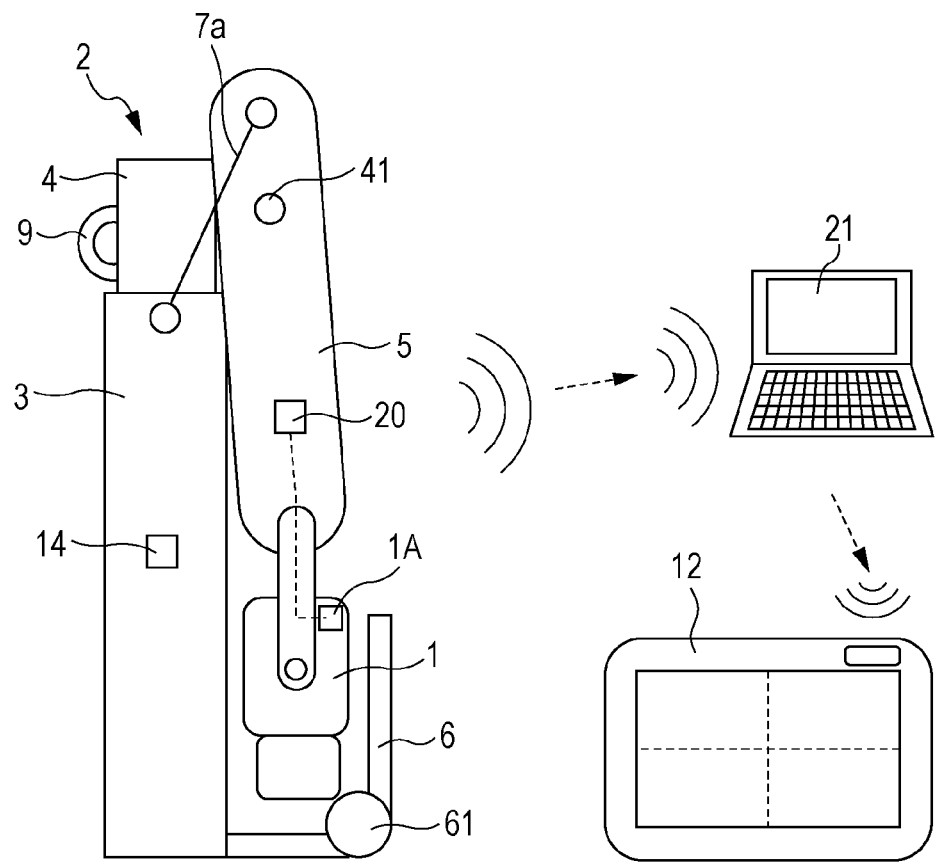
FIG. 20 illustrates an X-ray imaging apparatus according to a tenth embodiment of the present invention.

FIG. 20 illustrates a portable X-ray imaging apparatus according to a tenth embodiment of the present invention. The tenth embodiment is obtained by making a change to the ninth embodiment, specifically, by adding a function of inputting power to the X-ray-image detector 12 and a controller personal computer (PC) 21 in conjunction with the work of positioning the X-ray tube 1. Thus, the scope of the present invention is widened.

As in the ninth embodiment, the position detecting sensor 20 that detects the shape of the holding mechanism 2 or the position of the X-ray tube 1 is provided on the holding mechanism 2. The position detecting sensor 20 is in constant communication with the X-ray-image detector 12 and the controller PC 21. When the post movable portion 4 is lifted and the X-ray tube 1 has been moved from the tucked position to the imaging position, power is input to the X-ray-image detector 12 and the controller PC 21, whereby the X-ray imaging apparatus becomes ready for imaging. Since the worker can skip a step of inputting power to the X-ray-image detector 12 and the controller PC 21, the working efficiency in the X-ray imaging operation is increased.

Eleventh Embodiment

An eleventh embodiment of the present invention is obtained by making a change to the second embodiment, specifically, by adding a member that protects the X-ray tube 1. Thus, the scope of the present invention is widened.

The supporting foot 6 illustrated in FIG. 11 covers the X-ray tube 1 when the X-ray tube 1 is at the tucked position. Accordingly, the supporting foot 6 may also function as a protective plate that prevents and protect the X-ray tube 1 from interfering with peripheral elements when the X-ray imaging apparatus is carried or installed. By reducing the risk of interference between the X-ray tube 1 and peripheral elements, the portability of the apparatus is increased.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiments of the present invention, and by a method performed by the computer of the system or apparatus by, for example, reading out and executing the computer executable instructions from the storage medium to perform the functions of one or more of the above-described embodiments. The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-248612 filed on Nov. 12, 2012 and Japanese Patent Application No. 2013-073413 filed on Mar. 29, 2013, which are hereby incorporated by reference herein in their entirety.

What is claimed is:

1. A radiation generating device comprising:
    an arm configured to support a radiation generating unit that generates radiation;
    a post configured to support the arm;
    a movable portion configured to support the post and to be movable on a floor; and
    a supporting foot portion that is rotatable with respect to the movable portion.

2. The radiation generating device according to claim 1,
    wherein the arm is rotatable with respect to the post,
        wherein the supporting foot portion and the arm are operable to be placed in an open state and a closed state, and
    wherein, in a state where the supporting foot portion and the arm are closed, the supporting foot portion covers the radiation generating unit.

3. The radiation generating device according to claim 2, wherein, in the state where the supporting foot portion and the arm are closed, the radiation generating unit is positioned nearer to the floor than an upper end of the supporting foot portion.

4. The radiation generating device according to claim 2, wherein an axis of rotation of the supporting foot portion is parallel to an axis of rotation of the arm.

5. The radiation generating device according to claim 1, wherein the supporting foot portion is a plate-like member and includes a pad configured to support the radiation generating device by being in contact with the floor.

6. The radiation generating device according to claim 5, wherein the supporting foot portion includes a movable mechanism that is movable on the floor.

7. The radiation generating device according to claim 1, further comprising a supporting-foot hinge portion configured to connect the supporting foot portion and the movable portion to each other and to allow the supporting foot portion to be opened and closed with respect to the movable portion.

8. The radiation generating device according to claim 1, wherein the movable portion includes a wheel that is rotatable on the floor and a pad that supports the radiation generating device by being in contact with the floor.

9. The radiation generating device according to claim 1, wherein the arm and the post each include an extension mechanism and are each extendable and contractible.

10. The radiation generating device according to claim 9, wherein an extendable length of the arm that is allowed by the extension mechanism included in the arm is the same as an extendable length of the post that is allowed by the extension mechanism included in the post.

11. The radiation generating device according to claim 1, wherein the post includes a handle to be gripped by an operator.

12. The radiation generating device according to claim 1, further comprising a control unit configured to control the radiation generating unit to generate the radiation,
    wherein the control unit is provided at a position of the post or of the movable portion that is near the floor.

13. The radiation generating device according to claim 12, wherein the control unit includes a power supply unit configured to supply power to the radiation generating unit.

14. The radiation generating device according to claim 1, wherein the movable portion is part of the post.

15. The radiation generating device according to claim 1, wherein the radiation generating unit is of a transmission type.

16. The radiation generating device according to claim 1, further comprising:
    a rotational portion including
        a swivel hinge that allows the radiation generating unit to rotate about an axis that is parallel to a longitudinal direction of the arm, and
        a tilt hinge that allows the radiation generating unit to rotate about an axis that is perpendicular to the longitudinal direction of the arm.

17. A radiation imaging apparatus comprising:
    the radiation generating device according to claim 1;
    a detecting device configured to detect the radiation that has been transmitted through a subject and to output data on an image corresponding to the radiation; and
    a display device configured to display the image.

18. The radiation imaging apparatus according to claim 17, wherein the post includes a mechanism configured to forcibly stop extension of the post when the post reaches a position that a predetermined imaging distance is provided in accordance with a position and a posture of the subject.

19. The radiation imaging apparatus according to claim 17, wherein the post includes
    a mechanism configured to detect information on a position of the detecting device, and
    a mechanism configured to automatically stop extension of the post when the post reaches a position that a predetermined imaging distance is provided in accordance with a position of the detecting device.

20. The radiation imaging apparatus according to claim 17, further comprising a sensor configured to detect a position of the arm, wherein the radiation generating unit is turned off when the arm is closed with respect to the post.

21. The radiation imaging apparatus according to claim 17, further comprising a sensor configured to detect a position of the arm, wherein the radiation generating unit is turned on when the post is extended.

* * * * *